(12) United States Patent
Hammer

(10) Patent No.: US 11,857,417 B2
(45) Date of Patent: Jan. 2, 2024

(54) LEAFLET SUPPORT

(71) Applicant: Tal Hammer, Ramat Gan (IL)

(72) Inventor: Tal Hammer, Ramat Gan (IL)

(73) Assignee: TRILIO MEDICAL LTD., Or Yehuda (IL)

( * ) Notice: Subject to any disclaimer, the term of this patent is extended or adjusted under 35 U.S.C. 154(b) by 142 days.

(21) Appl. No.: 17/337,893

(22) Filed: Jun. 3, 2021

(65) Prior Publication Data

US 2022/0047388 A1    Feb. 17, 2022

Related U.S. Application Data

(60) Provisional application No. 63/066,268, filed on Aug. 16, 2020.

(51) Int. Cl.
    *A61F 2/24*    (2006.01)

(52) U.S. Cl.
    CPC .......... *A61F 2/2448* (2013.01); *A61F 2/2466* (2013.01); *A61F 2230/0006* (2013.01); *A61F 2230/0008* (2013.01)

(58) Field of Classification Search
    CPC .............................. A61F 2/2418; A61F 2/246
    See application file for complete search history.

(56) References Cited

U.S. PATENT DOCUMENTS

| | | |
|---|---|---|
| 4,423,525 A | 1/1984 | Vallana et al. |
| 4,493,329 A | 1/1985 | Crawford et al. |
| 4,625,727 A | 12/1986 | Leiboff |
| 4,778,468 A | 10/1988 | Hunt et al. |
| 4,853,986 A | 8/1989 | Allen |
| 5,108,420 A | 4/1992 | Marks |
| 5,330,521 A | 7/1994 | Cohen |
| 5,450,860 A | 9/1995 | O'Connor |
| 5,473,812 A | 12/1995 | Morris et al. |
| 5,776,178 A | 7/1998 | Pohndorf et al. |

(Continued)

FOREIGN PATENT DOCUMENTS

| | | | |
|---|---|---|---|
| CN | 111067666 A | * 4/2020 | ........... A61F 2/2412 |
| EP | 1759663 | 3/2007 | |

(Continued)

OTHER PUBLICATIONS

U.S. Appl. No. 63/066,268, filed Aug. 16, 2020.

(Continued)

*Primary Examiner* — Megan Y Wolf
*Assistant Examiner* — Cassidy N Stuhlsatz
(74) *Attorney, Agent, or Firm* — The Roy Gross Law Firm, LLC; Roy Gross

(57) ABSTRACT

A leaflet support for use with a native valve of a heart of a subject includes a frame that defines an array of adjoining cells, as well as an aperture between an upstream side and a downstream side of the frame. When placed against an annulus of the heart, the frame facilitates blood flow, via the cells, between the upstream side and the downstream side. The leaflet support further includes a barrier that is impermeable to blood flow, and that is coupled to the frame in a manner that obstructs blood flow through the aperture. The leaflet support further includes ventricular legs, that each extend radially outward and upstream, toward the frame. Other embodiments are also described.

30 Claims, 25 Drawing Sheets

(56) References Cited

U.S. PATENT DOCUMENTS

| | | | |
|---|---|---|---|
| 5,792,400 A | 8/1998 | Talja et al. |
| 5,843,120 A | 12/1998 | Israel et al. |
| 5,957,953 A | 9/1999 | DiPoto et al. |
| 6,027,523 A | 2/2000 | Schmieding |
| 6,298,272 B1 | 10/2001 | Peterfeso et al. |
| 6,299,635 B1 | 10/2001 | Frantzen |
| 6,332,893 B1 | 12/2001 | Mortier et al. |
| 6,575,976 B2 | 6/2003 | Grafton |
| 6,613,078 B1 | 9/2003 | Barone |
| 6,613,079 B1 | 9/2003 | Wolinsky et al. |
| 6,616,684 B1 | 9/2003 | Vidlund et al. |
| 6,626,899 B2 | 9/2003 | Houser et al. |
| 6,626,930 B1 | 9/2003 | Allen et al. |
| 6,629,921 B1 | 10/2003 | Schweich, Jr. et al. |
| 6,641,597 B2 | 11/2003 | Burkhart et al. |
| 6,702,846 B2 | 3/2004 | Mikus et al. |
| 6,723,038 B1 | 4/2004 | Schroeder et al. |
| 6,730,118 B2 | 5/2004 | Spenser et al. |
| 6,797,001 B2 | 9/2004 | Mathis et al. |
| 6,884,250 B2 | 4/2005 | Monassevitch et al. |
| 6,908,478 B2 | 6/2005 | Alferness et al. |
| 7,041,097 B1 | 5/2006 | Webler |
| 7,101,395 B2 | 9/2006 | Tremulis et al. |
| 7,125,421 B2 | 10/2006 | Tremulis et al. |
| 7,144,363 B2 | 12/2006 | Pai et al. |
| 7,159,593 B2 | 1/2007 | McCarthy et al. |
| 7,169,187 B2 | 1/2007 | Datta et al. |
| 7,175,625 B2 | 2/2007 | Culbert |
| 7,186,262 B2 | 3/2007 | Saadat |
| 7,201,772 B2 | 4/2007 | Schwammenthal et al. |
| 7,311,728 B2 | 12/2007 | Solem et al. |
| 7,316,706 B2 | 1/2008 | Bloom et al. |
| 7,316,710 B1 | 1/2008 | Cheng et al. |
| 7,338,506 B2 | 3/2008 | Caro |
| 7,351,256 B2 | 4/2008 | Hojeibane et al. |
| 7,390,329 B2 | 6/2008 | Westra et al. |
| 7,530,995 B2 | 5/2009 | Quijano et al. |
| 7,547,321 B2 | 6/2009 | Silvestri et al. |
| 7,549,983 B2 | 6/2009 | Roue et al. |
| 7,618,449 B2 | 11/2009 | Tremulis et al. |
| 7,628,797 B2 | 12/2009 | Tieu et al. |
| 7,632,303 B1 | 12/2009 | Stalker et al. |
| 7,635,329 B2 | 12/2009 | Goldfarb et al. |
| 7,666,204 B2 | 2/2010 | Thornton et al. |
| 7,771,467 B2 | 8/2010 | Svensson |
| 7,780,726 B2 | 8/2010 | Seguin |
| 7,803,187 B2 | 9/2010 | Hauser |
| 7,871,433 B2 | 1/2011 | Lattouf |
| 7,988,725 B2 | 8/2011 | Gross et al. |
| 7,991,484 B1 | 8/2011 | Sengupta et al. |
| 7,993,368 B2 | 8/2011 | Gambale et al. |
| 8,010,207 B2 | 8/2011 | Smits et al. |
| 8,029,518 B2 | 10/2011 | Goldfarb et al. |
| 8,043,360 B2 | 10/2011 | McNamara et al. |
| 8,052,592 B2 | 11/2011 | Goldfarb et al. |
| 8,108,054 B2 | 1/2012 | Helland |
| 8,142,493 B2 | 3/2012 | Spence et al. |
| 8,236,013 B2 | 8/2012 | Chu |
| 8,262,724 B2 | 9/2012 | Seguin et al. |
| 8,262,725 B2 | 9/2012 | Subramanian |
| 8,267,981 B2 | 9/2012 | Boock et al. |
| 8,323,335 B2 | 12/2012 | Rowe et al. |
| 8,332,051 B2 | 12/2012 | Sommer et al. |
| 8,475,525 B2 | 7/2013 | Maisano et al. |
| 8,628,571 B1 | 1/2014 | Hacohen et al. |
| 8,961,594 B2 | 2/2015 | Maisano et al. |
| 9,044,246 B2 | 6/2015 | Goldfarb et al. |
| 9,358,371 B2 | 6/2016 | McNamara et al. |
| 2002/0032481 A1 | 5/2002 | Gabbay |
| 2002/0151961 A1 | 10/2002 | Lashinski et al. |
| 2002/0177904 A1 | 11/2002 | Huxel et al. |
| 2003/0167071 A1 | 9/2003 | Martin et al. |
| 2003/0229350 A1 | 12/2003 | Kay |
| 2003/0236568 A1 | 12/2003 | Hojeibane et al. |
| 2004/0024451 A1 | 2/2004 | Johnson et al. |
| 2004/0181287 A1 | 9/2004 | Gellman |
| 2004/0186566 A1 | 9/2004 | Hindrichs et al. |
| 2004/0193092 A1 | 9/2004 | Deal |
| 2004/0199183 A1 | 10/2004 | Oz et al. |
| 2004/0236419 A1 | 11/2004 | Milo |
| 2004/0260389 A1 | 12/2004 | Case et al. |
| 2005/0016560 A1 | 1/2005 | Voughlohn |
| 2005/0090827 A1 | 4/2005 | Gedebou |
| 2005/0107812 A1 | 5/2005 | Starksen et al. |
| 2005/0107871 A1 | 5/2005 | Realyvasquez et al. |
| 2005/0177228 A1 | 8/2005 | Solem et al. |
| 2005/0203606 A1 | 9/2005 | VanCamp |
| 2005/0216039 A1 | 9/2005 | Lederman |
| 2005/0256532 A1 | 11/2005 | Nayak et al. |
| 2006/0052821 A1 | 3/2006 | Abbot et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0178700 A1 | 8/2006 | Quinn |
| 2006/0229708 A1 | 10/2006 | Powell et al. |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0021781 A1 | 1/2007 | Jervis et al. |
| 2007/0038221 A1 | 2/2007 | Fine et al. |
| 2007/0038293 A1 | 2/2007 | St. Goar et al. |
| 2007/0049942 A1 | 3/2007 | Hindrichs et al. |
| 2007/0049970 A1 | 3/2007 | Belef et al. |
| 2007/0061010 A1 | 3/2007 | Hauser et al. |
| 2007/0066863 A1 | 3/2007 | Rafiee et al. |
| 2007/0093869 A1 | 4/2007 | Bloom et al. |
| 2007/0118151 A1 | 5/2007 | Davidson |
| 2007/0162107 A1 | 7/2007 | Haug et al. |
| 2007/0198082 A1 | 8/2007 | Kapadia et al. |
| 2007/0203391 A1 | 8/2007 | Bloom et al. |
| 2007/0239265 A1* | 10/2007 | Birdsall ............... A61L 27/34 |
| | | 623/2.11 |
| 2007/0250160 A1 | 10/2007 | Rafiee |
| 2007/0276437 A1 | 11/2007 | Call et al. |
| 2007/0282375 A1 | 12/2007 | Hindrichs et al. |
| 2008/0003539 A1 | 1/2008 | Lundgren |
| 2008/0035160 A1 | 2/2008 | Woodson et al. |
| 2008/0077231 A1 | 3/2008 | Heringes et al. |
| 2008/0221672 A1* | 9/2008 | Lamphere ........... A61F 2/2439 |
| | | 623/2.12 |
| 2008/0262609 A1 | 10/2008 | Gross et al. |
| 2008/0275469 A1 | 11/2008 | Fanton et al. |
| 2008/0288044 A1 | 11/2008 | Osborne |
| 2008/0288062 A1 | 11/2008 | Andrieu et al. |
| 2008/0300629 A1 | 12/2008 | Surti |
| 2009/0084386 A1 | 4/2009 | McClellan et al. |
| 2009/0118776 A1 | 5/2009 | Kelsch et al. |
| 2009/0149872 A1 | 6/2009 | Gross et al. |
| 2009/0171439 A1 | 7/2009 | Nissl |
| 2009/0216265 A1 | 8/2009 | DeVries |
| 2009/0222081 A1 | 9/2009 | Linder et al. |
| 2009/0254103 A1 | 10/2009 | Deutsch |
| 2009/0259307 A1 | 10/2009 | Gross et al. |
| 2009/0264995 A1 | 10/2009 | Subramanian |
| 2009/0326648 A1 | 12/2009 | Machold et al. |
| 2010/0121349 A1 | 5/2010 | Meier et al. |
| 2010/0130992 A1 | 5/2010 | Machold et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168791 A1 | 7/2010 | Kassab et al. |
| 2010/0174358 A1 | 7/2010 | Rabkin et al. |
| 2010/0185278 A1 | 7/2010 | Schankereli |
| 2010/0204662 A1 | 8/2010 | Orlov et al. |
| 2010/0211166 A1 | 8/2010 | Miller et al. |
| 2010/0217382 A1 | 8/2010 | Chau et al. |
| 2010/0234935 A1 | 9/2010 | Bashiri et al. |
| 2010/0249908 A1 | 9/2010 | Chau et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |

(56) References Cited

U.S. PATENT DOCUMENTS

| | | |
|---|---|---|
| 2010/0324598 A1 | 12/2010 | Anderson |
| 2011/0022164 A1 | 1/2011 | Quinn et al. |
| 2011/0029066 A1 | 2/2011 | Gilad |
| 2011/0035000 A1 | 2/2011 | Nieminen et al. |
| 2011/0054519 A1* | 3/2011 | Neuss .............. A61B 17/12177 606/213 |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0184510 A1 | 7/2011 | Maisano |
| 2011/0238088 A1 | 9/2011 | Bolduc et al. |
| 2011/0238112 A1 | 9/2011 | Kim et al. |
| 2011/0251678 A1 | 10/2011 | Eidenschink et al. |
| 2011/0264208 A1 | 10/2011 | Duffy et al. |
| 2012/0022633 A1 | 1/2012 | Olson et al. |
| 2012/0022640 A1 | 1/2012 | Gross et al. |
| 2012/0035712 A1 | 2/2012 | Maisano |
| 2012/0215236 A1 | 8/2012 | Matsunaga et al. |
| 2012/0232373 A1 | 9/2012 | Hallander et al. |
| 2012/0296349 A1 | 11/2012 | Smith et al. |
| 2013/0030522 A1 | 1/2013 | Rowe et al. |
| 2013/0035759 A1* | 2/2013 | Gross ...................... A61F 2/246 623/2.38 |
| 2013/0325115 A1 | 12/2013 | Maisano et al. |
| 2015/0119979 A1 | 4/2015 | Maisano et al. |
| 2016/0030166 A1 | 2/2016 | Kapadia |
| 2016/0199181 A1* | 7/2016 | Kramer ................. A61F 2/2418 623/2.17 |
| 2016/0331523 A1 | 11/2016 | Chau et al. |
| 2017/0095331 A1* | 4/2017 | Spenser ................. A61F 2/2439 |
| 2017/0273789 A1 | 9/2017 | Yaron et al. |
| 2018/0049874 A1 | 2/2018 | Baldwin et al. |
| 2018/0243086 A1 | 8/2018 | Barbarino et al. |
| 2018/0325661 A1 | 11/2018 | Delgado et al. |
| 2018/0353181 A1 | 12/2018 | Wei |
| 2019/0053903 A1 | 2/2019 | Rohl et al. |
| 2019/0069991 A1 | 3/2019 | Metchik et al. |
| 2019/0099267 A1* | 4/2019 | Tubishevitz .......... A61F 2/2427 |
| 2020/0060849 A1* | 2/2020 | Inouye ............. A61B 17/12177 |

FOREIGN PATENT DOCUMENTS

| | | | |
|---|---|---|---|
| EP | 1 836 971 | 9/2007 | |
| WO | 1992/005093 | 4/1992 | |
| WO | 2005/021063 | 3/2005 | |
| WO | 2005/102194 | 11/2005 | |
| WO | 2006/091163 | 8/2006 | |
| WO | 2006/097931 | 9/2006 | |
| WO | 2008/068756 | 6/2008 | |
| WO | 2009/080801 | 7/2009 | |
| WO | 2009/101617 | 8/2009 | |
| WO | 2010/004546 | 1/2010 | |
| WO | 2010/071494 | 6/2010 | |
| WO | 2010/073246 | 7/2010 | |
| WO | 2010/128502 | 11/2010 | |
| WO | 2010/128503 | 11/2010 | |
| WO | 2011/051942 | 5/2011 | |
| WO | 2011/089601 | 7/2011 | |
| WO | 2011/143263 | 11/2011 | |
| WO | 2012/127309 | 9/2012 | |
| WO | 2013/114214 A2 | 8/2013 | |
| WO | WO-2014150106 A1 * | 9/2014 | ......... A61B 17/0057 |
| WO | 2018/050200 | 3/2018 | |
| WO | 2018/178977 | 10/2018 | |

OTHER PUBLICATIONS

Shikhar Agarwal et al., "Interventional Cardiology Perspective of Functional Tricuspid Regurgitation," Circulatoin: Cardiovascular Interventions, pp. 565-573; Dec. 2009; vol. 2, Issue 6.

* cited by examiner

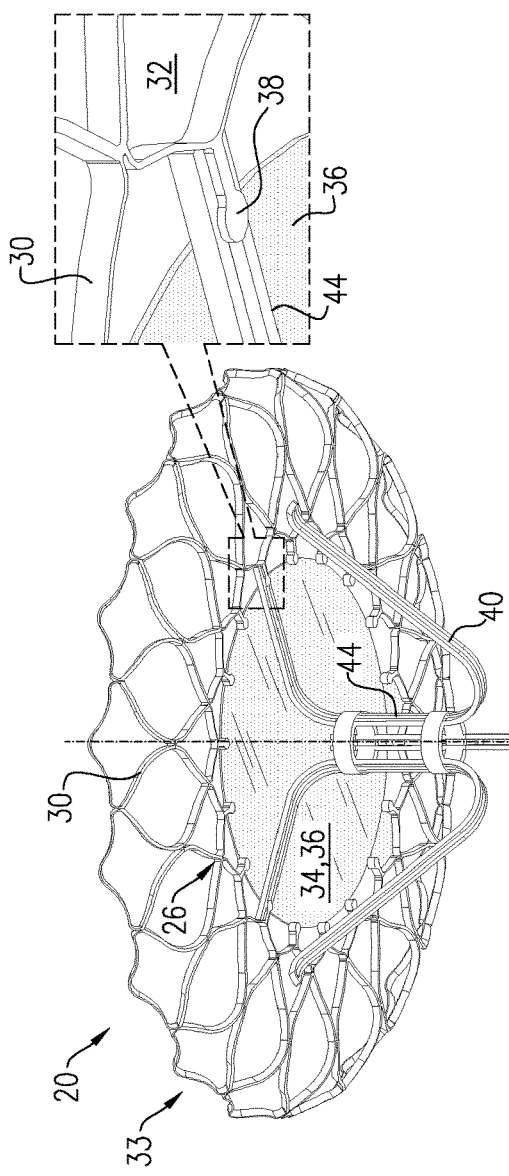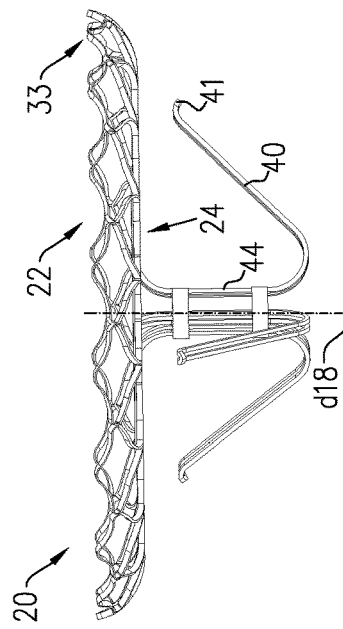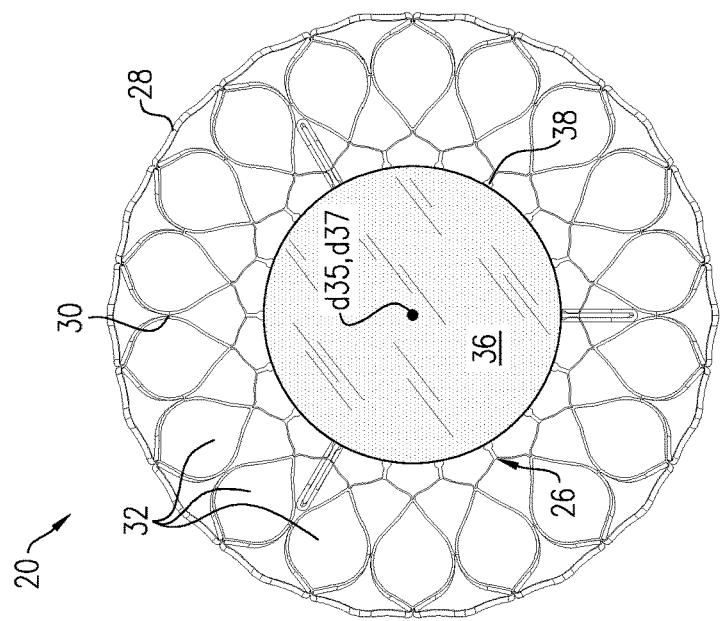

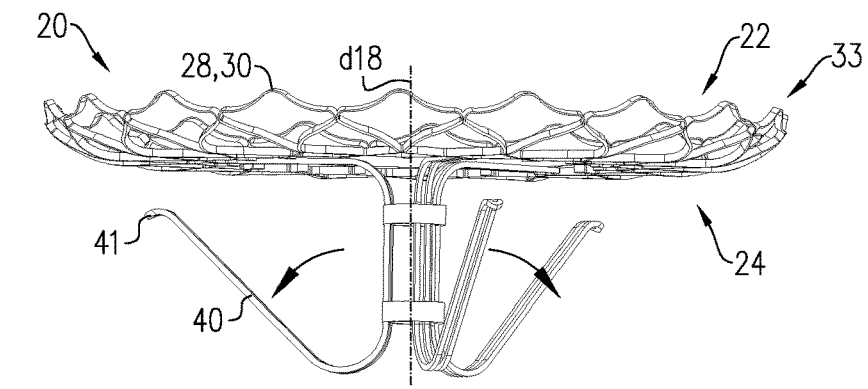
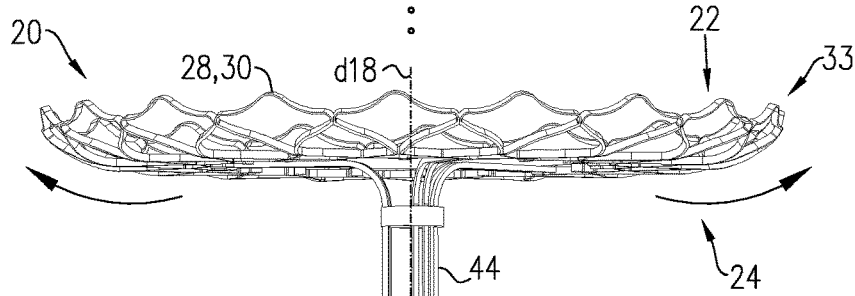
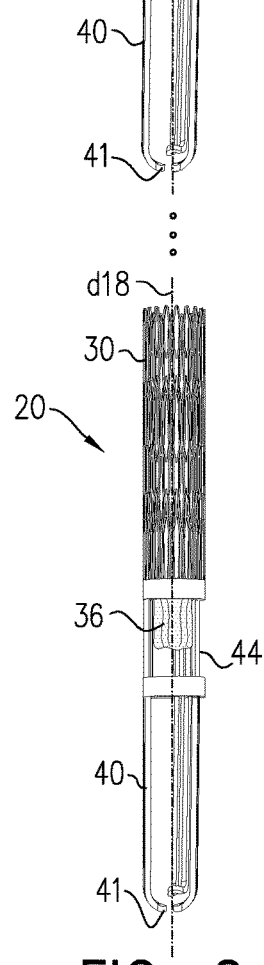
FIG. 2
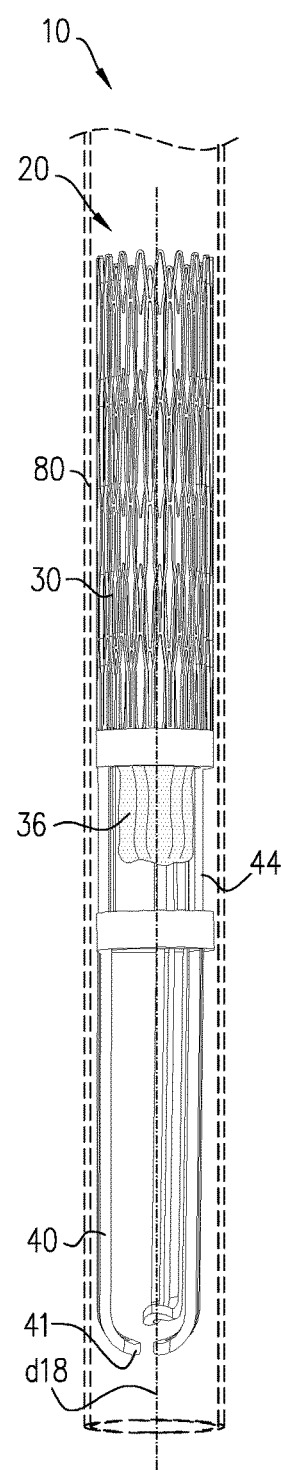
FIG. 3

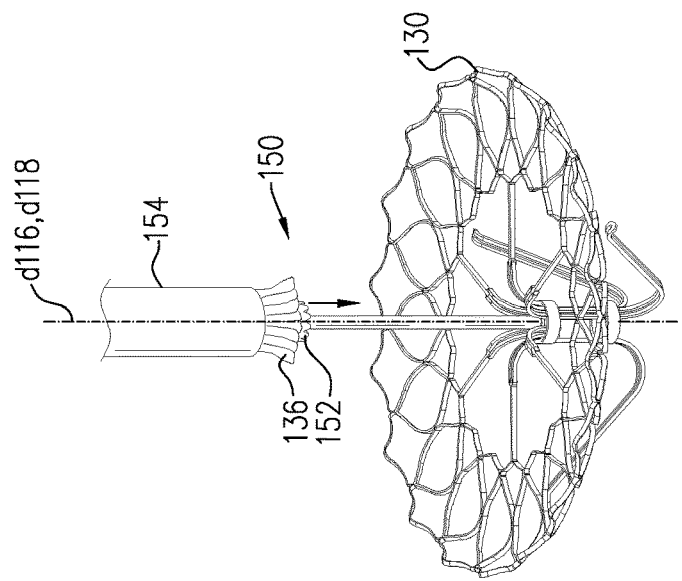
FIG. 7B
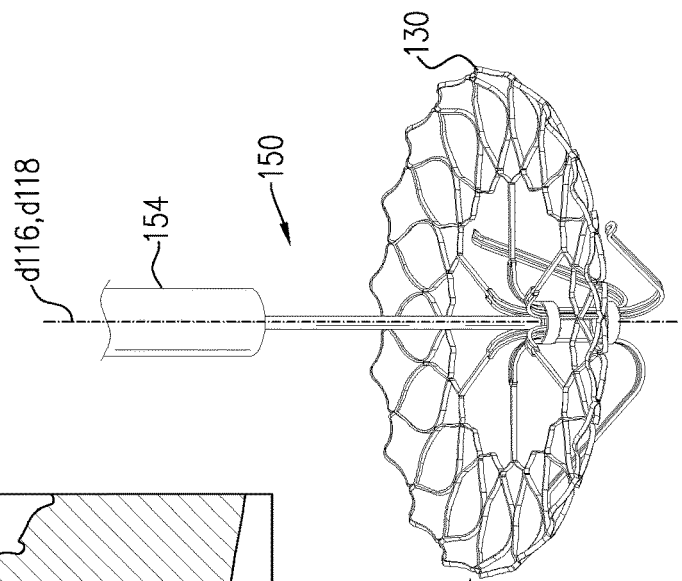
FIG. 7A
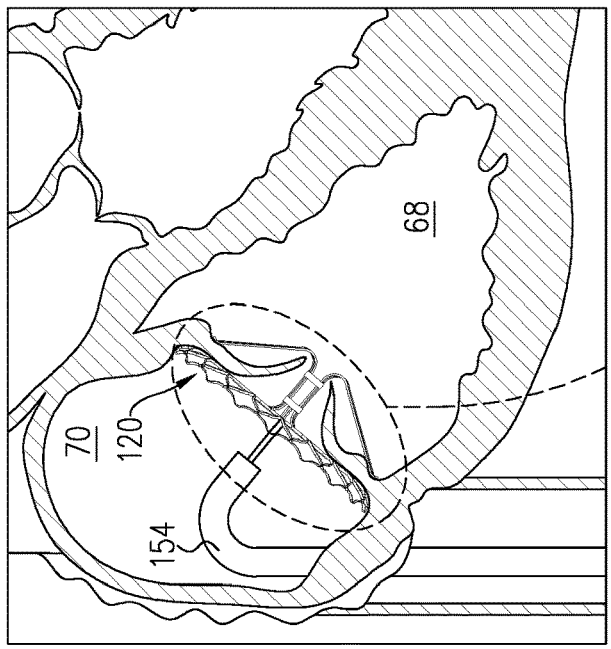

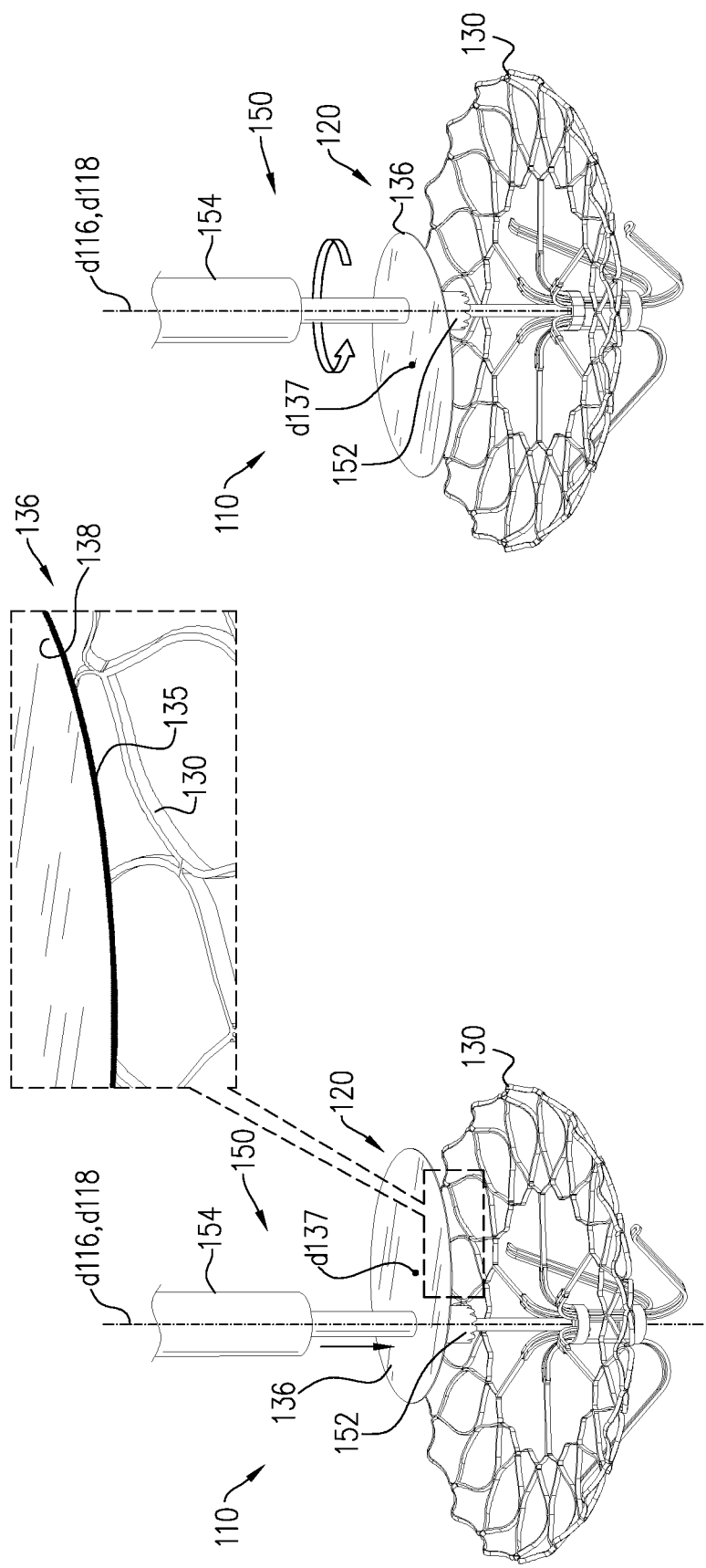

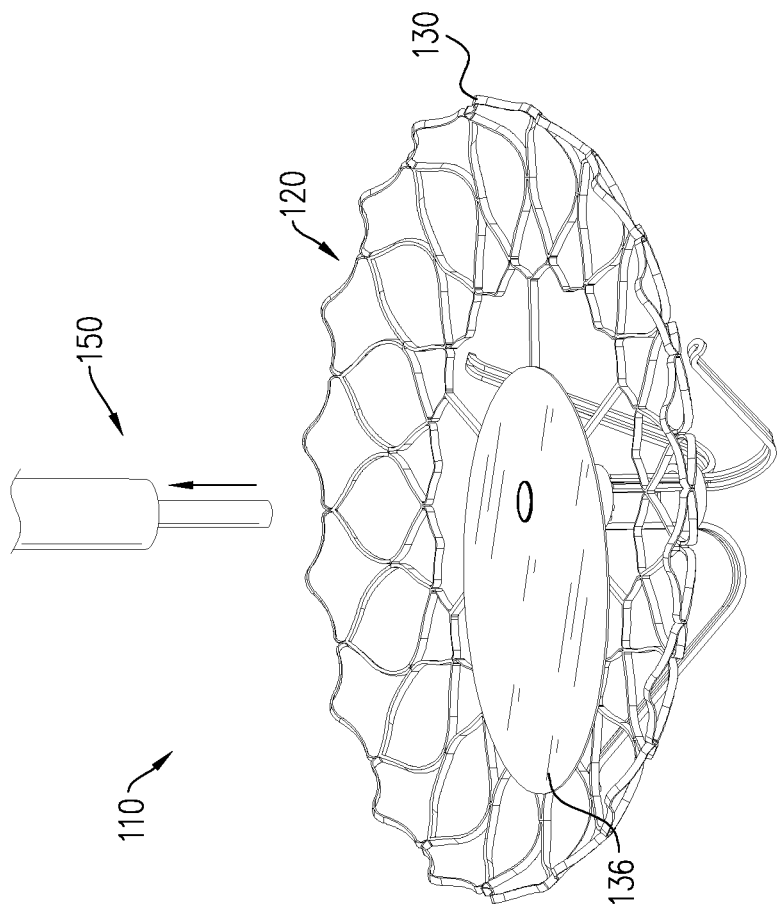
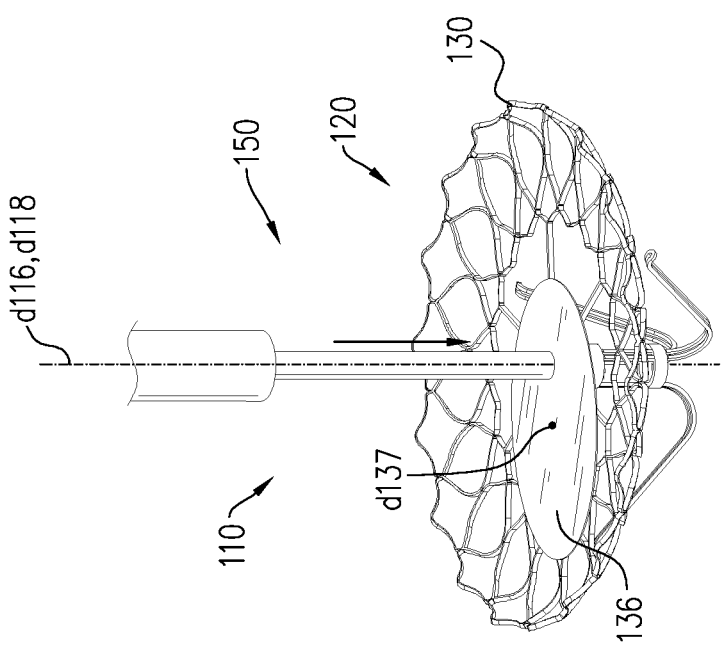
FIG. 7E
FIG. 7F

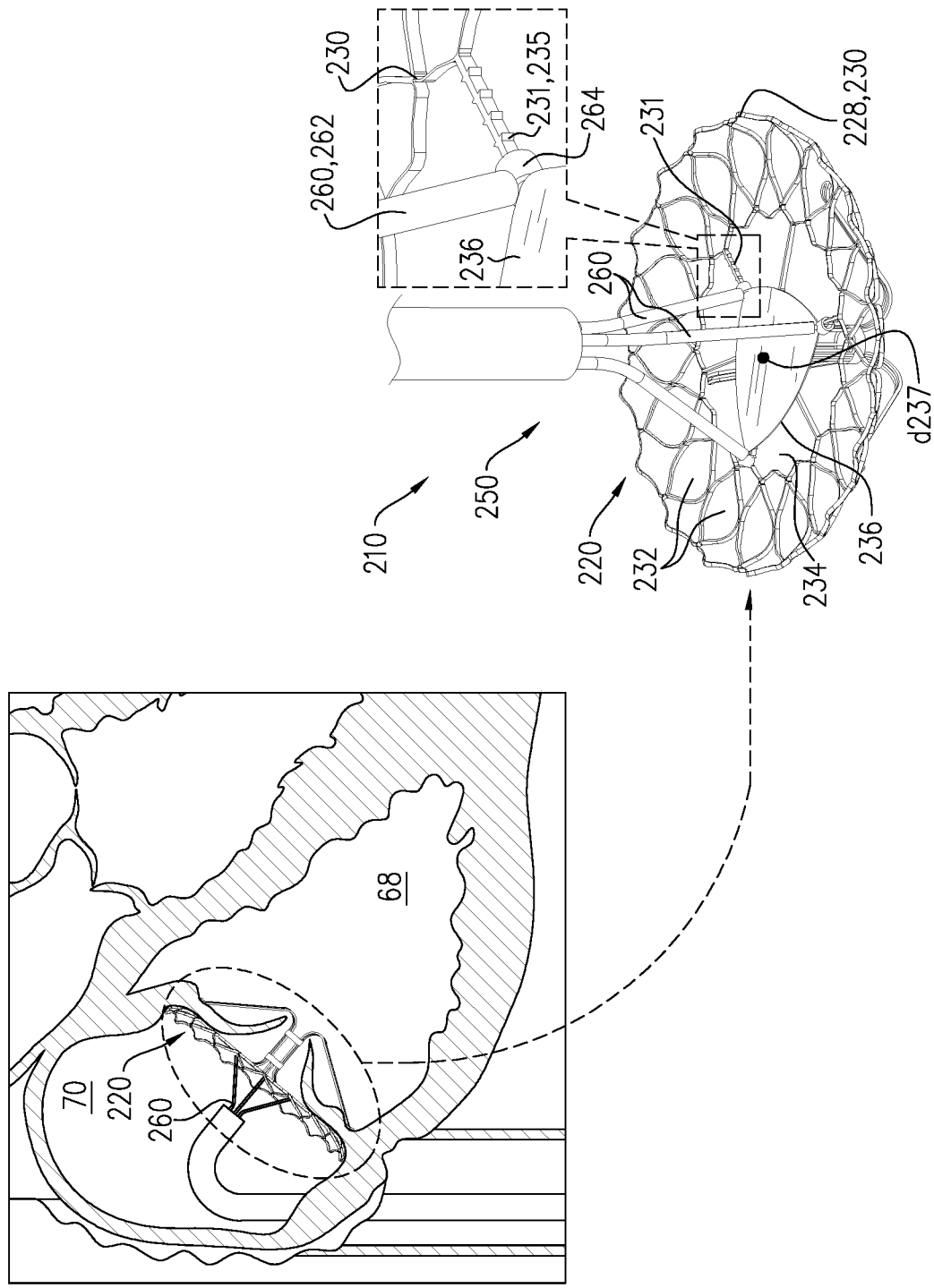

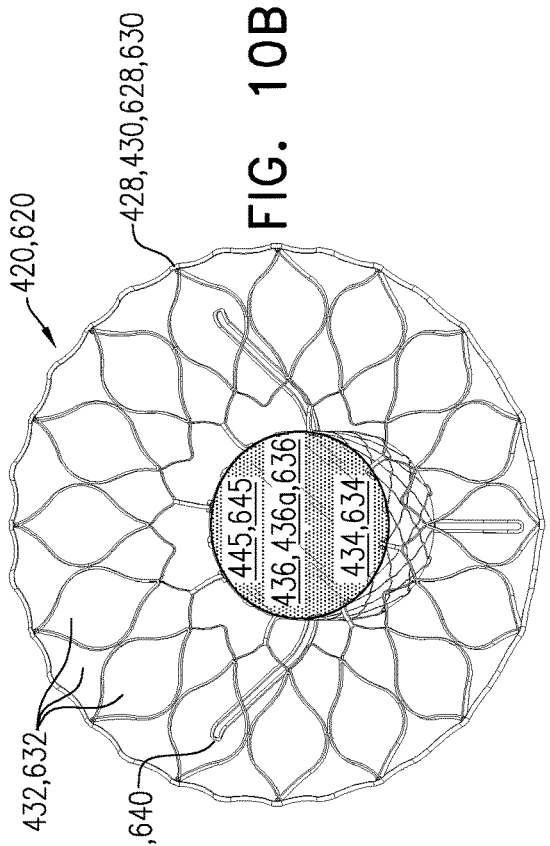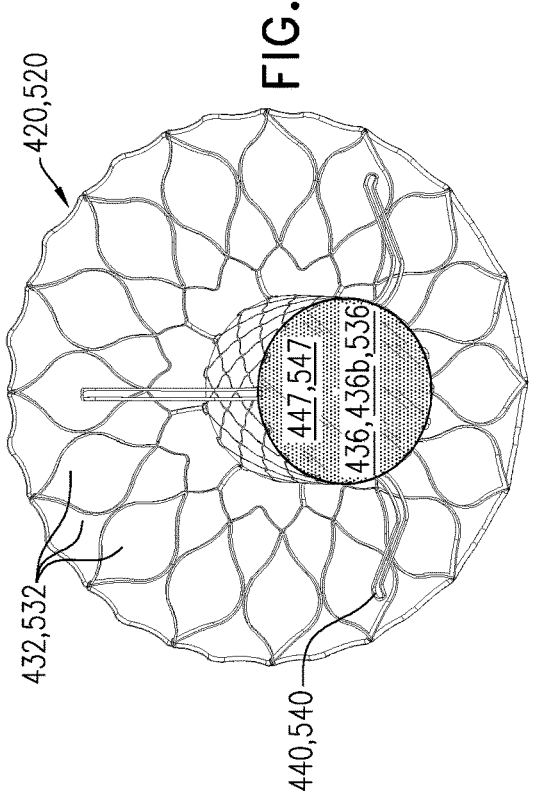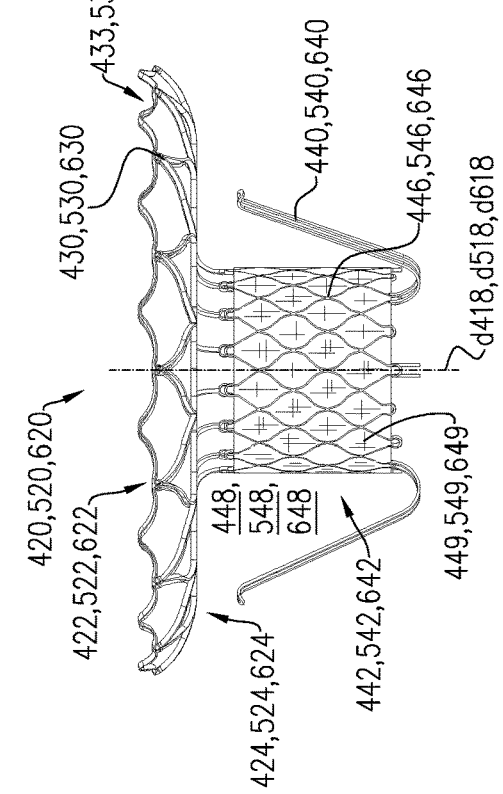

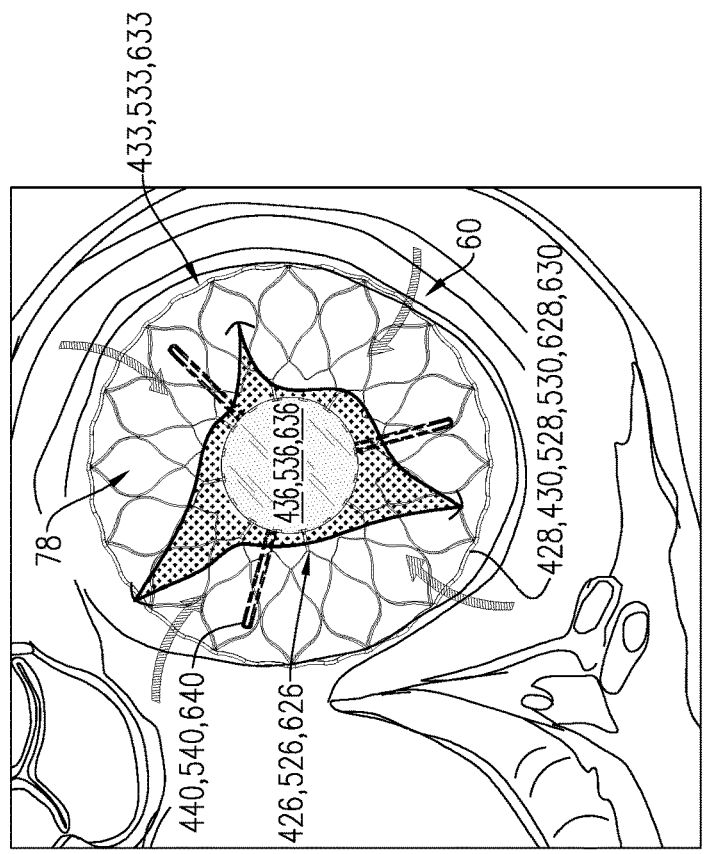
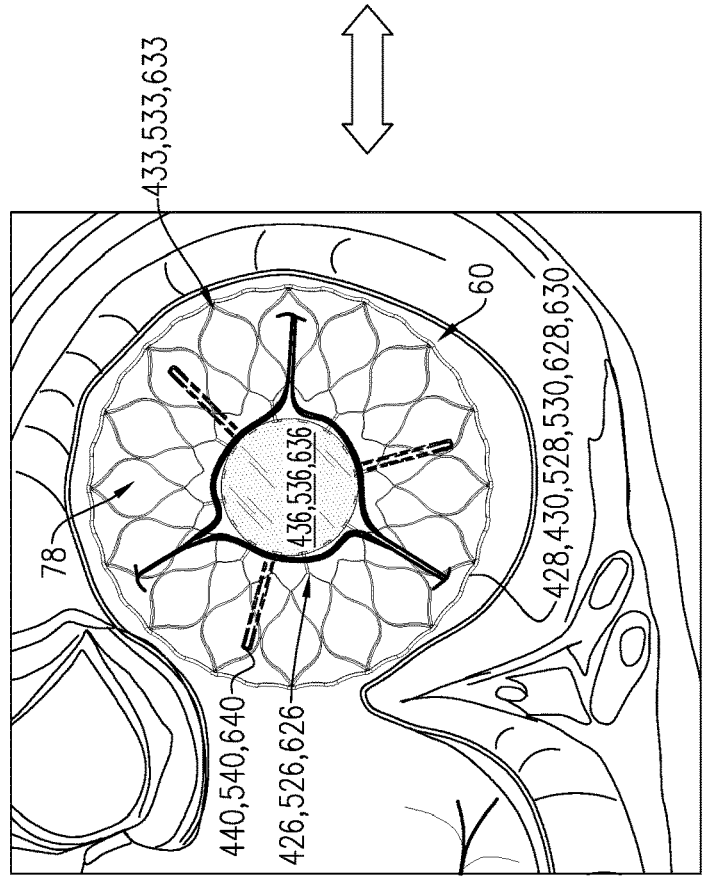
FIG. 14

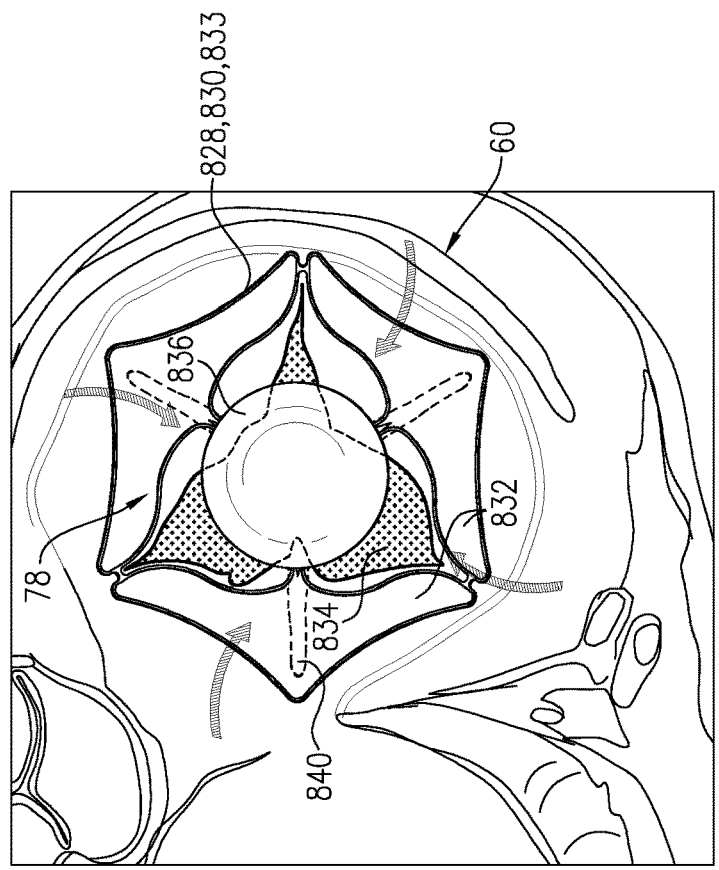
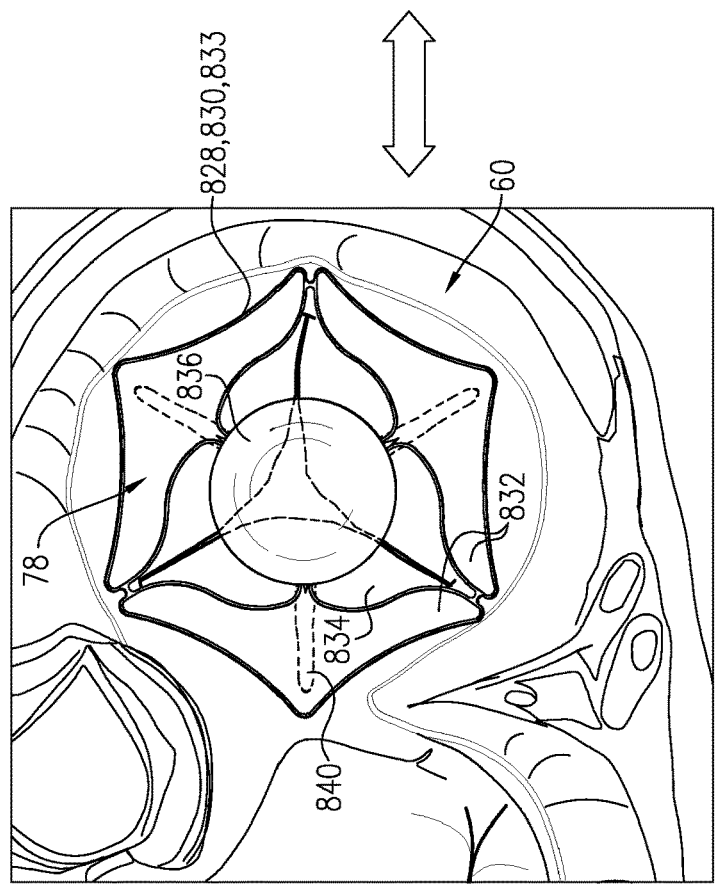
FIG. 19

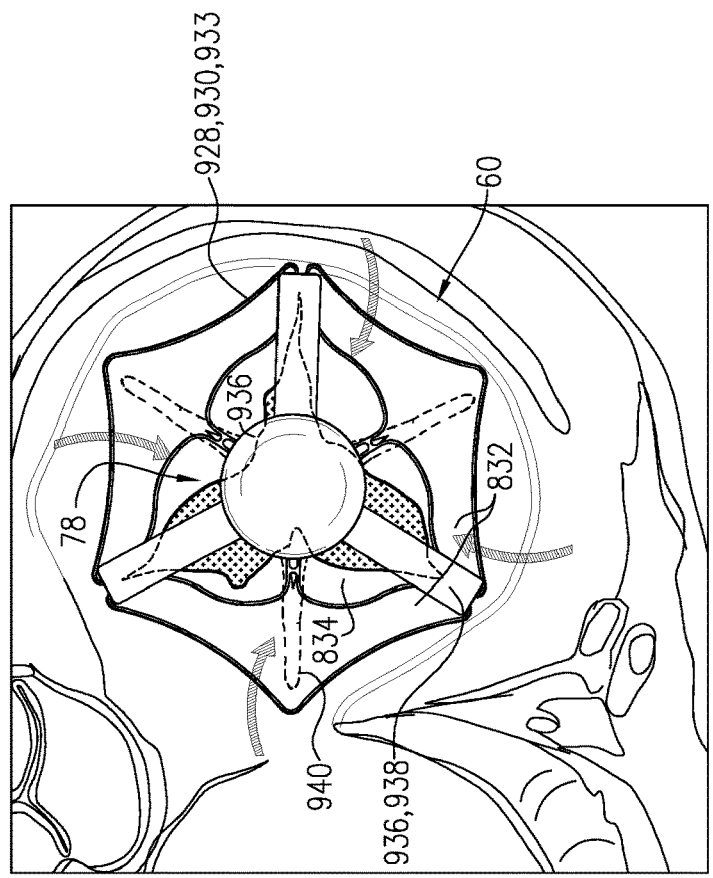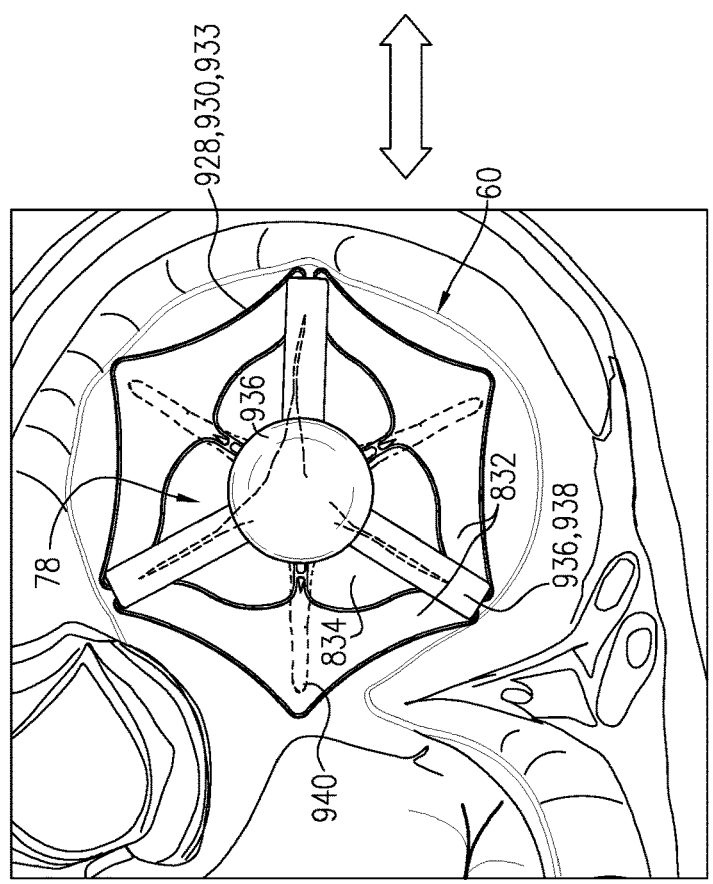
FIG. 21

LEAFLET SUPPORT

CROSS REFERENCE TO RELATED APPLICATIONS

The present application claims priority from U.S. Provisional Application 63/066,268, filed Aug. 16, 2020, entitled, "LEAFLET SUPPORT," which is incorporated herein by reference.

FIELD OF THE INVENTION

Some applications of the present invention relate in general to cardiac implants. More specifically, some applications of the present invention relate to supports for leaflets of a native heart valve.

BACKGROUND

Dilation of the annulus of a heart valve, such as that caused by ischemic heart disease, prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

Applications of the present invention are directed to apparatus and methods for use of a leaflet support with a native valve of a heart of a subject. The leaflet support comprises a frame that typically defines an array of cells and an aperture. The leaflet support further comprises a barrier that is coupled to the frame such that the barrier obstructs blood flow, e.g., blood flow through the frame and/or through the aperture. For some applications, the frame is ring-shaped, such that an inner ring-perimeter defines the aperture.

For some applications, the frame comprises a plurality of aperture-surrounding struts that extend radially inwardly and in a downstream direction from an outer frame-perimeter of the frame. For some such applications, at least two aperture-surrounding struts surround the aperture.

For some applications, the aperture is defined at a center of the leaflet support. Alternatively, the aperture may be offset with respect to the leaflet support. Similarly, the barrier may be either centrally located or offset with respect to leaflet support.

For some applications, the barrier covers a portion of the aperture. For some such applications, aspects of the present invention include an adjustment tool configured to change the portion of the aperture area covered by the barrier. For example, the adjustment tool may change the portion of the aperture area covered by the barrier transluminally, while the leaflet support is disposed at the native valve.

For some applications, the barrier covers a portion of the array of cells. For some such applications, the barrier defines at least one radial strip that extends between a central axis of the leaflet support and the outer frame-perimeter.

For some applications, the leaflet support comprises a first barrier and a second barrier, each barrier coupled to the frame. Typically for such applications, the first barrier is spaced apart from the second barrier in a manner that facilitates blood flow through the frame between the first barrier and the second barrier.

For some applications, the leaflet support is fastened to the native valve by placing the frame against an annulus of the native valve. Typically for such applications, the leaflet support facilitates blood flow, via the frame, between an upstream side of the frame and a downstream side of the frame. For some such applications, the frame has an annulus-fitting zone that is concavely shaped to fit the annulus of the native valve.

For some applications, the support is provided with the barrier pre-coupled to the frame. Alternatively, the barrier may be coupled to the frame after the frame has been fastened to the native valve. For some such applications, aspects of the present invention include a barrier-delivery tool configured to transluminally couple the barrier to the frame. For example, the barrier-delivery tool may position the barrier with respect to the frame, and couple the barrier to the frame in a manner that obstructs blood flow through the aperture.

Typically, the leaflet support comprises ventricular legs that extend radially outward and upstream, toward the frame. For some applications, respective leg end-portions face the frame from a position radially outward of the aperture.

For some such applications, respective leg end-portions face the frame from downstream of the frame. For example, the leg end-portions may face the frame from a position radially outward of the barrier.

For some such applications, at least in absence of tissue between ventricular legs and the frame, respective leg end-portions may extend upstream of the frame. For example, the leg end-portions may contact the barrier.

For some such applications, the legs are distributed evenly around a central axis. Alternatively, some of the legs may be disposed closer to certain legs than they are to other legs.

For some applications, the leaflet support comprises a tubular portion that supports the barrier. For some such applications, the barrier covers an upstream end and/or a downstream end of the tubular portion.

For some such applications, the leaflet support obstructs blood flow through both the tubular portion and the aperture. For example, the tubular portion may be covered by a circumferential sleeve that is impervious to blood flow.

For some such applications, the tubular portion couples the legs to each other and to the frame. For example, the leaflet support may define a circumferential space between the legs and the tubular portion, within which, while the leaflet support is implanted at the native valve, native leaflets of the native valve may deflect as the heart cycles ventricular systole and ventricular diastole.

For some applications, the leaflet support is fastened to the native valve by tissue of the native valve being squeezed between the frame and the legs. For some such applications, the barrier obstructs blood flow through the frame, such that blood may flow antegrade between the native leaflets, radially outward of the frame.

There is therefore provided, in accordance with an application of the present invention, an apparatus for use with a native valve of a heart of a subject, the apparatus including a leaflet support, the leaflet support including:
    a frame having an upstream side and a downstream side, the frame:
        defining an array of adjoining cells, and an aperture between the upstream side and the downstream side, and configured to:

be placed against an annulus of the heart, and facilitate blood flow, via the cells, between the upstream side and the downstream side;

a barrier:
- impermeable to blood flow, and
- coupled to the frame in a manner that obstructs blood flow through the aperture; and a plurality of ventricular legs, each ventricular leg extending radially outward and upstream, toward the frame.

In an application, each of the ventricular legs is coupled to the frame.

In an application, each ventricular leg extends further radially outward than the barrier.

In an application, the frame and the ventricular legs include an elastic shape-memory material.

In an application, the leaflet support has a compressed state and an expanded state, such that:
- while the leaflet support is in the compressed state, the leaflet support is transluminally deliverable to the heart, and
- while the leaflet support is in the expanded state, the frame extends radially outward from the aperture.

In an application, the aperture is a first aperture, and the frame defines a second aperture between the upstream side and the downstream side.

In an application, a greatest width of the frame is between 10 mm and 100 mm.

In an application, the greatest width of the frame is less than 60 mm.

In an application, the greatest width of the frame is greater than 40 mm.

In an application:
- the aperture is a first aperture,
- the frame is shaped to define a second aperture between the upstream side and the downstream side, and
- the frame includes a plurality of aperture-surrounding struts, at least two of the struts surrounding the first aperture and at least two of the struts surrounding the second aperture, the struts extending radially inwardly and in a downstream direction from an outer frame-perimeter of the frame.

In an application, each ventricular leg extends radially outward from exactly two of the aperture-surrounding struts.

In an application, for a given ventricular leg:
- a first one of the exactly two of the aperture-surrounding struts surrounds the first aperture in part, and
- a second one of the exactly two of the aperture-surrounding struts surrounds the second aperture in part.

In an application, each ventricular leg extends radially outward from a downstream end of at least one of the aperture-surrounding struts.

In an application, each ventricular leg extends, from a downstream end of at least one of the aperture-surrounding struts:
- radially outward, and
- toward the frame.

In an application, a respective end-portion of each ventricular leg faces the frame from a position that is:
- radially outward of the barrier, and
- downstream from the frame.

In an application, in an absence of tissue between the ventricular legs and the frame, a respective end-portion of each ventricular leg is disposed upstream from the frame.

In an application, in an absence of tissue between the ventricular legs and the barrier, a respective end-portion of each ventricular leg presses against the barrier.

In an application, the barrier is coupled to the frame in a manner that at least partially covers at least one of the cells.

In an application, the barrier is coupled to the frame in a manner that at least partially covers a plurality of the cells of the frame.

In an application, the barrier is coupled to the frame in a manner that at least partially covers each cell of the frame.

In an application:
- the frame defines an outer frame-perimeter, and
- the barrier is shaped to define at least one radial strip, the at least one radial strip extending radially inwardly toward a central axis of the leaflet support and radially outwardly toward the outer frame-perimeter.

In an application, the at least one radial strip extends at least two thirds of a radial distance from the central axis to the outer frame-perimeter.

In an application, the at least one radial strip is a plurality of the radial strips.

In an application, the plurality of the radial strips includes exactly three of the radial strips.

In an application, the plurality of the radial strips are positioned to each align with a respective commissure of the native valve of the heart of the subject and to reduce flailing of native leaflets of the heart into an atrium of the heart.

In an application:
- the aperture defines an aperture area, and
- the barrier obstructs blood flow through the aperture by covering a portion of the aperture area.

In an application, the apparatus includes an adjustment tool, the adjustment tool being configured to, while the leaflet support is disposed at the native valve, transluminally adjust a portion of the aperture area covered by the barrier.

In an application, the adjustment tool is configured to, while the leaflet support is disposed at the native valve, transluminally reposition the portion of the aperture area covered by the barrier.

In an application, the adjustment tool is configured to, while the leaflet support is disposed at the native valve, transluminally resize the portion of the aperture area covered by the barrier.

In an application:
- the barrier includes an adjustment lock, and
- the adjustment tool is configured to transluminally change the portion of the aperture area covered by the barrier by:
  - engaging the adjustment lock, and
  - transferring a force to the adjustment lock.

In an application:
- the frame includes a sizing strut, and
- transfer of the force, from the adjustment tool to the adjustment lock, causes radial motion of the adjustment lock along the sizing strut, thereby changing the portion of the aperture area covered by the barrier.

In an application, the apparatus includes a barrier-delivery tool, the barrier-delivery tool configured to:
- reversibly engage the barrier, and
- while the frame is disposed at the native valve, transluminally:
  - position the barrier with respect to the frame, and
  - couple the barrier to the frame in the manner that obstructs blood flow through the aperture.

In an application, the barrier-delivery tool is configured to reversibly connect to the frame.

In an application, the barrier includes:
a barrier-frame including a shape-memory material, and
a flexible sheet, the sheet fixedly attached to the barrier-frame such that the sheet obstructs blood flow through the barrier-frame,
and the barrier has:
a transluminally-deliverable compressed state in which the barrier-frame has a compressed width, and
an expanded state in which the barrier-frame has an expanded width that is greater than the compressed width.

In an application, the barrier-delivery tool is configured to reversibly engage the barrier in a manner that facilitates rotation of the barrier about a central axis of the delivery tool.

In an application, the barrier defines a frame-fitting portion, the frame-fitting portion dimensioned to snugly engage the frame.

In an application, the barrier defines the frame-fitting portion at a portion of the barrier that is radially outward from a center-point of the barrier.

In an application, the barrier-delivery tool is configured to reversibly engage the barrier in a manner that facilitates rotation of the barrier about the frame-fitting portion.

In an application, the barrier is a first barrier, and the leaflet support includes a second barrier coupled to the frame, and spaced apart from the first barrier in a manner that facilitates blood flow, through the frame, between the first barrier and the second barrier.

In an application, the leaflet support includes exactly two barriers.

In an application, the leaflet support includes a third barrier coupled to the frame, the third barrier being spaced apart from the first barrier and from the second barrier in a manner that facilitates blood flow, through the frame, between (i) the third barrier and the first barrier, and (ii) the third barrier and the second barrier.

In an application, the frame has an annulus-fitting zone that is dimensioned to fit the annulus of the native valve.

In an application, the annulus-fitting zone is concave in an upstream direction.

In an application, the barrier is planar.

In an application, the barrier is circular or elliptical.

In an application, the barrier is "D"-shaped.

In an application, a central axis of the leaflet support passes through the aperture.

In an application, the central axis passes through a center point of the aperture.

In an application, each of the ventricular legs is disposed at a respective position that is radially equidistant from the central axis.

In an application, the ventricular legs are distributed evenly around the central axis.

In an application, two of the ventricular legs are disposed closer to each other than they are to a third ventricular leg.

In an application, the barrier is coupled to the frame such that the central axis passes through the barrier.

In an application, the barrier is coupled to the frame such that the central axis passes through the center of the barrier.

In an application, the plurality of ventricular legs includes at least three ventricular legs.

In an application, the plurality of ventricular legs includes exactly three ventricular legs.

In an application, the barrier is a flexible sheet.

In an application, the flexible sheet includes an elastic material.

In an application, the flexible sheet includes a fabric.

In an application, the flexible sheet includes a polymer.

In an application, the adjoining cells of the array are arranged to shape the frame as a ring having an inner ring-perimeter that defines the aperture.

In an application, each ventricular leg extends radially outward than the inner ring-perimeter.

In an application, the leaflet support has a compressed state and an expanded state, such that:
while the leaflet support is in the compressed state, the leaflet support is transluminally deliverable to the heart, and
while the leaflet support is in the expanded state, the ring is disposed radially outward from the aperture.

In an application, a greatest width of the ring is greater than 10 mm, and less than 100 mm.

In an application, the greatest width of the ring is less than 90 mm.

In an application, the greatest width of the ring is less than 80 mm.

In an application, the greatest width of the ring is less than 70 mm.

In an application, the greatest width of the ring is less than 60 mm.

In an application, the greatest width of the ring is less than 50 mm.

In an application, the greatest width of the ring is less than 40 mm.

In an application, the greatest width of the ring is less than 30 mm.

In an application, the greatest width of the ring is less than 20 mm.

In an application, a greatest width of the ring is less than 100 mm.

In an application, the greatest width of the ring is greater than 20 mm.

In an application, the greatest width of the ring is greater than 30 mm.

In an application, the greatest width of the ring is greater than 40 mm.

In an application, the greatest width of the ring is greater than 50 mm.

In an application, the greatest width of the ring is greater than 60 mm.

In an application, the greatest width of the ring is greater than 70 mm.

In an application, the greatest width of the ring is greater than 80 mm.

In an application, the greatest width of the ring is greater than 90 mm.

In an application:
the aperture defines an aperture area, and
the barrier covers 10-100 percent of the aperture area.

In an application, the barrier covers the entire aperture area.

In an application, the barrier covers at least 20 percent of the aperture area.

In an application, the barrier covers at least 30 percent of the aperture area.

In an application, the barrier covers at least 40 percent of the aperture area.

In an application, the barrier covers at least 50 percent of the aperture area.

In an application, the barrier covers at least 60 percent of the aperture area.

In an application, the barrier covers at least 70 percent of the aperture area.

In an application, the barrier covers at least 80 percent of the aperture area.

In an application, the barrier covers at least 90 percent of the aperture area.

In an application, the barrier covers less than 90 percent of the aperture area.

In an application, the barrier covers less than 80 percent of the aperture area.

In an application, the barrier covers less than 70 percent of the aperture area.

In an application, the barrier covers less than 60 percent of the aperture area.

In an application, the barrier covers less than 50 percent of the aperture area.

In an application, the barrier covers less than 40 percent of the aperture area.

In an application, the barrier covers less than 30 percent of the aperture area.

In an application, the barrier covers less than 20 percent of the aperture area.

In an application, the leaflet support includes a tubular portion that:
defines a circumferential wall,
couples the plurality of ventricular legs to each other and to the frame, and
supports the barrier in a manner that obstructs blood flow through the aperture.

In an application, the apparatus includes a circumferential sleeve, the circumferential sleeve:
impermeable to blood flow, and
coupled to the circumferential wall in a manner that obstructs blood flow through the circumferential wall.

In an application, the tubular portion couples the plurality of ventricular legs to the frame at the inner ring-perimeter.

In an application, the tubular portion includes an elastic shape-memory material.

In an application, each ventricular leg extends from the tubular portion:
radially outward, and
upstream toward the frame,
such that the leaflet support defines a circumferential space that circumscribes the circumferential wall and is disposed radially inwardly from the ventricular legs and downstream of the downstream side.

In an application, each ventricular leg extends, from the tubular portion, further radially outward than the barrier.

In an application, each ventricular leg extends, from the tubular portion, further radially outward than the inner ring-perimeter.

In an application, the circumferential wall circumscribes a central axis of the leaflet support.

In an application, the central axis passes through the aperture.

In an application, the central axis passes through a center point of the aperture.

In an application, the barrier is coupled to the frame such that the central axis passes through the barrier.

In an application, the barrier is coupled to the frame such that the central axis passes through a center point of the barrier.

In an application, the tubular portion is coupled to the frame such that the tubular portion is disposed downstream of the frame.

In an application, the tubular portion is connected to the inner ring-perimeter.

In an application:
a cross-section of the tubular portion defines a tubular area,
a cross-section of the aperture defines an aperture area, and the tubular area is 80-120% of the aperture area.

In an application, the tubular area is equal to the aperture area.

In an application, the tubular portion supports the barrier in a manner that obstructs blood flow through the tubular portion.

In an application:
the tubular portion defines an upstream end and a downstream end, such that the circumferential wall extends between the upstream end and the downstream end,
a circumferential sleeve covers the circumferential wall, and
the barrier covers at least one end of the tubular portion selected from the group consisting of: the upstream end and the downstream end.

In an application, the barrier covers both the upstream end and the downstream end.

In an application, the barrier covers the upstream end but not the downstream end.

In an application, the barrier covers the downstream end but not the upstream end.

In an application, the apparatus includes a connecting portion, the connecting portion:
disposed downstream of the aperture, and
connecting each of the ventricular legs to the frame, such that each ventricular leg extends, from the connecting portion:
radially outward, and
upstream toward the frame.

In an application, a respective end-portion of each ventricular leg faces the frame from a position that is:
radially outward of the barrier, and
downstream from the frame.

In an application, a respective end-portion of each ventricular leg faces the frame from a position that is:
radially outward of the inner ring-perimeter, and
downstream from the frame.

In an application, in an absence of tissue between ventricular legs and the ring, a respective end-portion of each ventricular leg is disposed upstream from the frame.

In an application, in an absence of tissue between ventricular legs and the barrier, a respective end-portion of each ventricular leg presses against the barrier.

In an application, the connecting portion connects each of the ventricular legs to the frame at the inner ring-perimeter.

In an application, the connecting portion and the barrier are each coupled to the frame at a shared site of the frame.

In an application, the connecting portion and the barrier are each coupled to the frame at the inner ring-perimeter.

In an application, the barrier is coupled to the frame in a manner that obstructs blood flow through a cell of the frame.

In an application, the barrier is coupled to the frame in a manner that obstructs blood flow through a plurality of the cells of the frame.

In an application, the barrier is coupled to the frame in a manner that obstructs blood flow through all of the cells of the frame.

In an application, the connecting portion and the barrier are each coupled to the frame at a shared site of the frame.

In an application, the connecting portion and the barrier are each coupled to the frame at the inner ring-perimeter.

There is further provided, in accordance with an application of the present invention, a method for use with a native valve disposed between an atrium and a ventricle of a heart of a subject, the method including:
 translumially advancing, to the heart, a leaflet support, the leaflet support including:
  a frame, the frame:
   having an upstream side and a downstream side, and defining:
    an array of adjoining cells, and
    an aperture between the upstream side and the downstream side;
  a barrier, the barrier being:
   impermeable to blood flow, and
   coupled to the frame; and
 implanting the leaflet support at the native valve, such that:
  the frame is placed against an annulus of the native valve, and
  during ventricular diastole:
   blood flows from the atrium to the ventricle via the cells, and
   the barrier obstructs blood flow through the aperture.

In an application, implanting the leaflet support at the native valve includes implanting the leaflet support at the native valve such that the barrier is disposed in the atrium.

In an application:
 the barrier covers a portion of an aperture area, and
 the method includes:
  translumially advancing, to the heart, an adjustment tool; and
  using the adjustment tool, transferring a force to the barrier such that the force changes the portion of the aperture area that is covered by the barrier.

There is further provided, in accordance with an application of the present invention, a method for use with a native valve disposed between an atrium and a ventricle of a heart of a subject, the method including:
 translumially advancing, to the heart, a frame:
  having an upstream side and a downstream side, and defining:
   an array of adjoining cells, and
   an aperture between the upstream side and the downstream side;
 implanting the frame at the native valve, such that:
  the frame is placed against an annulus of the native valve, and
  during ventricular diastole, blood flows from the atrium to the ventricle via the frame;
 translumially advancing, to the heart, a barrier that is impermeable to blood flow; and
 subsequently to the implanting of the frame, coupling the barrier to the frame, such that the barrier obstructs blood flow through the aperture.

In an application, the step of translumially advancing the barrier is performed subsequently to the implanting of the frame.

There is further provided, in accordance with an application of the present invention, a method for use with a native valve disposed between an atrium and a ventricle of a heart of a subject, and having a plurality of leaflets, the method including:
 translumially advancing, to the heart, a leaflet support, the leaflet support including:
  a frame, the frame defining an array of adjoining cells arranged to shape the frame as a ring, the ring:
   having an upstream side and a downstream side, and
   defining an aperture between the upstream side and the downstream side,
  a barrier, the barrier being:
   impermeable to blood flow, and
   coupled to the frame,
  a plurality of ventricular legs, each ventricular leg extending radially outward and upstream, toward the frame; and implanting the leaflet support at the native valve, such that:
   the barrier is disposed upstream of the leaflets,
   the leaflets are squeezed between the frame and the legs, and
   during ventricular diastole:
    blood flows from the atrium, around the support and between the leaflets, into the ventricle, and
    the barrier obstructs blood flow through the frame.

The present invention will be more fully understood from the following detailed description of applications thereof, taken together with the drawings, in which:

BRIEF DESCRIPTION OF THE DRAWINGS

FIGS. 1A-C are schematic illustrations showing perspective views of a leaflet support, in accordance with some applications of the invention;

FIG. 2 is a schematic illustration showing the leaflet support in an expanded state, and in a compressed state suitable for transluminal delivery, in accordance with some applications of the present invention;

FIG. 3 is a schematic illustration showing a system comprising the leaflet support and a delivery tool, in accordance with some applications of the present invention;

FIGS. 7A-F are schematic illustrations showing use of a system comprising a barrier-delivery tool and a leaflet support, in accordance with some applications of the invention;

FIGS. 8A-C are schematic illustrations showing use of a system comprising a leaflet support and an adjustment tool, in accordance with some applications of the invention;

FIGS. 10A-C are schematic illustrations showing perspective views of other leaflet supports, in accordance with some applications of the present invention;

FIGS. 13-14 are schematic illustrations showing leaflet supports implanted at the tricuspid valve, in accordance with some applications of the present invention;

FIG. 19 includes schematic illustrations showing the leaflet support implanted at the tricuspid valve, in accordance with some applications of the present invention;

FIG. 21 includes schematic illustrations showing the leaflet support implanted at the tricuspid valve, in accordance with some applications of the present invention.

DETAILED DESCRIPTION OF EMBODIMENTS

Figure 4A:
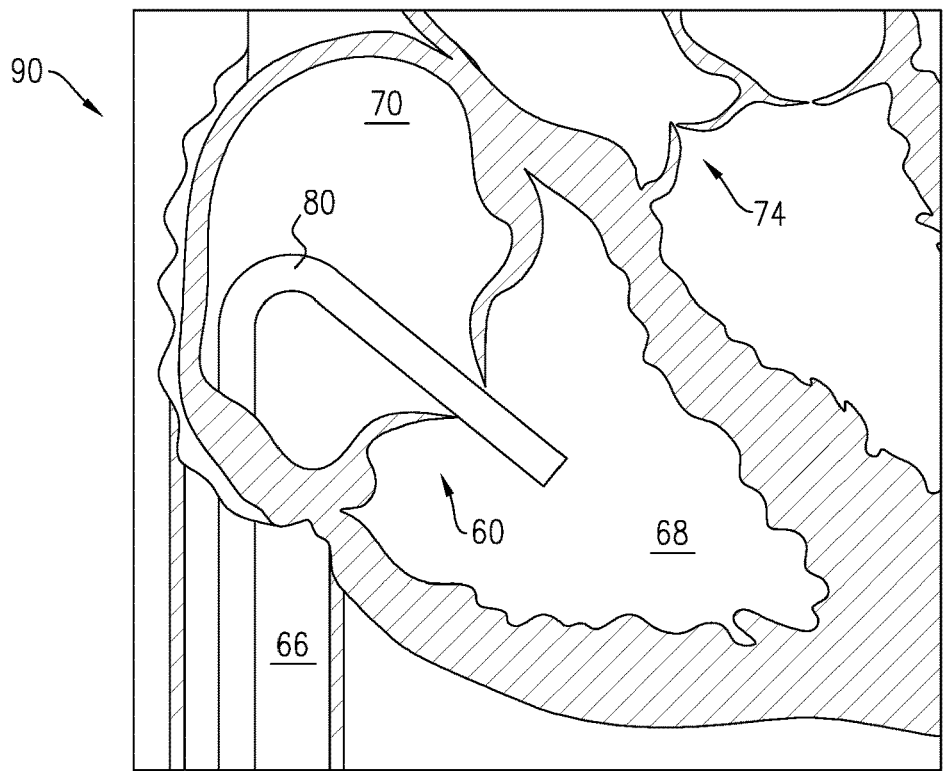
FIGS. 4A-F are schematic illustrations showing the leaflet support being implanted at a tricuspid valve of a heart, in accordance with some applications of the present invention.

Reference is made to FIGS. 1A-C, which are schematic illustrations showing perspective views of a leaflet support 20, in accordance with some applications of the invention.

As shown, leaflet support 20 comprises a ring-shaped frame 30 that defines an array of adjoining cells 32. The ring formed by frame 30 extends radially outward from an aperture 34 that is defined by an inner ring-perimeter 26, to an outer ring-perimeter 28. For some applications, aperture 34 is central with respect to leaflet support 20 (e.g., with respect to outer ring-perimeter 28 of frame 30). That is, for such applications, a central axis d18 of leaflet support 20 passes through aperture 34 (e.g., through a center point d35 of the aperture).

For some applications, an annulus-fitting zone 33 of leaflet support 20 is concavely shaped. For example, and as shown in FIG. 1C, annulus-fitting zone 33 may be shaped as a spherical segment. Alternatively or in addition, annulus-fitting zone 33 may be frustoconical.

Typically, each cell 32, and therefore frame 30 as a whole, is configured to facilitate passage of blood therethrough, such that when leaflet support 20 is implanted within a heart 90 of a subject, blood may flow between an upstream side 22 and a downstream side 24 of the frame.

For some applications, and as shown, each cell 32 is defined by frame 30, without other elements within the cell. It is hypothesized by the inventors that cells 32 being defined solely by the frame: (i) facilitates passage of blood through the cells, and (ii) reduces the amount of material required to define the cells.

For some applications, and as shown, adjoining cells 32 form a series of geometric patterns. For some such applications, and as shown, the series of geometric patterns is repeated circumferentially about frame 30. It is hypothesized by the inventors that cells 32 forming a repeating series of geometric patterns: (i) facilitates distribution of external forces applied to frame 30, among the cells, and (ii) increases likelihood that different portions of frame 30 will react similarly to the application of external forces.

Leaflet support 20 further comprises a barrier 36 that is impermeable to blood flow. For some applications, and as shown, barrier 36 is a flexible sheet. For example, barrier 36 may comprise a sheet (e.g., a fabric and/or a polymer, such as a polymer fabric). Alternatively, barrier 36 may comprise an ex-vivo-derived or in-vitro-derived tissue, such as pericardium. Barrier 36 is coupled (e.g., fixedly coupled, such as by stitching or by gluing) to frame 30 such that the barrier obstructs blood flow through aperture 34.

For some applications, barrier 36 is planar (e.g., disc-shaped). For example, and as shown in FIGS. 1A-1B, barrier 36 may be shaped as a circular disc. Alternatively, barrier 36 may be shaped as an oval disc. Alternatively still, barrier 36 may be shaped as a "D"-shaped disc.

For some applications, and as shown, barrier 36 is centrally located with respect to leaflet support 20. That is, central axis d18 of the support passes through barrier 36. For some such applications, and as shown, central axis d18 passes through a center point d37 of barrier 36.

For some applications, and as shown, aperture 34 is centrally located with respect to leaflet support 20. That is, central axis d18 of the support passes through aperture 34. For some such applications, and as shown, central axis d18 passes through a center point d35 of aperture 34. For example, central axis d18 may pass through both center point d35 of aperture 34, as well as center point d37 of barrier 36.

Typically, barrier 36 and aperture 34 at least partially overlap, e.g., such that barrier 36 covers at least 10 percent (e.g., at least 20 percent, e.g., at least 30 percent, e.g., at least 40 percent, e.g., at least 50 percent, e.g., at least 60 percent, e.g., at least 70 percent, e.g., at least 80 percent, e.g., at least 90 percent) and/or up to 100 percent (e.g., up to 90 percent, e.g., up to 80 percent, e.g., up to 70 percent, e.g., up to 60 percent, e.g., up to 50 percent, e.g., up to 40 percent, e.g., up to 30 percent, e.g., up to 20 percent) of the cross-sectional area of the aperture. For example, barrier 36 may cover the aperture entirely. For some applications, barrier 36 covers an area greater than aperture area. For example, barrier 36 may be larger than the aperture, and/or may extend radially outward further than an inner ring-perimeter 26, e.g., such that the barrier covers at least some of frame 30 (e.g., covering at least a portion of at least one of the cells defined by the frame).

For some applications, and as shown, barrier 36 does not cover cells 32 of frame 30, e.g., such that barrier 36 is disposed only radially inward from inner ring-perimeter 26. For example, and as shown in the inset of FIG. 1B, barrier 36 may be coupled to frame 30 via fasteners 38.

Leaflet support 20 further comprises a plurality of ventricular legs 40 (e.g., three legs, as shown). For some applications, each ventricular leg 40 is coupled to frame 30 (e.g., at inner ring-perimeter 26). For some such applications, ventricular legs 40 and barrier 36 are each coupled to the frame at a shared site of frame 30.

For some applications and as shown, legs 40 are connected to frame 30 via a connecting portion 44 disposed downstream of aperture 34. Typically for such applications, connecting portion 44 also connects each leg 40 to the other legs. For some applications, and as shown in FIG. 1B, connecting portion 44 and barrier 36 are each coupled to frame 30 at a shared site of the frame (e.g., at inner ring-perimeter 26).

For some applications, and as shown, legs 40 are spaced evenly from central axis d18. That is, legs 40 are positioned to be radially equidistant from central axis d18.

For some applications, and as shown, legs 40 are arranged evenly about central axis d18. For some applications, radial arrangement of legs 40 around central axis d18 is determined responsively to anatomy of a given native valve (e.g., a tricuspid valve 60 or a mitral valve 74) at which support 20 is to be implanted. For some such applications, two legs 40 may be disposed radially closer to each other than they are to a third leg. For example, legs 40 may be arranged such that two legs may be positioned under a posterior leaflet 63 of mitral valve 74, and the third leg may be positioned under an anterior leaflet 61 of the mitral valve. Alternatively, legs 40 may be arranged such that each respective leg may be positioned under an anterior leaflet, posterior leaflet or a septal leaflet of tricuspid valve 60.

Typically, each leg 40 extends (e.g., from connecting portion 44) both radially outward, and upstream toward frame 30. For some applications, and as shown, end-portions 41 of legs 40 do not reach frame 30. Typically for such applications, each respective end-portion 41 faces frame 30 (e.g., from a position that is (i) radially outward of barrier 36 and/or inner ring-perimeter 26; and (ii) downstream of frame 30.

Reference is made to FIG. 2, which includes schematic illustrations showing leaflet support 20 in an expanded state, and in a compressed state suitable for transluminal delivery, in accordance with some applications of the invention.

For some applications, leaflet support 20 (e.g., frame 30 and/or legs 40 thereof) comprises an elastic shape-memory material (e.g., Nitinol), such that upon removal of external constraining forces, leaflet support 20 automatically expands into the expanded state. As shown in upper frame of FIG. 2, while support 20 is in the expanded state, the ring formed by frame 30 typically extends radially outward (e.g., from connecting portion 44).

For some applications, and as shown, while leaflet support 20 is in the compressed state (lower frame of FIG. 2), ventricular legs 40 extend downstream from connecting portion 44, and/or frame 30 assumes a tubular shape extending upstream from the connecting portion. For example, cells 32 may become narrower as frame 30 assumes the tubular shape. For some such applications, boundaries of at least some of cells 32 may come into contact with each other as frame 30 assumes the tubular shape.

For some applications in which frame 30 assumes a tubular shape while leaflet support 20 is compressed into the compressed state, frame 30 assumes the tubular shape around barrier 36, such that the barrier is disposed within a lumen defined by the tubular shape.

Reference is made to FIG. 3, which is a schematic illustration showing system 10 comprising leaflet support 20 and delivery tool 80, in accordance with some applications of the invention. As shown, FIG. 3 shows leaflet support 20, in the compressed state, disposed within delivery tool 80 for transluminal (e.g., transfemoral) delivery to heart 90.

Reference is made to FIGS. 4A-F, which are schematic illustrations showing leaflet support 20 being implanted at tricuspid valve 60 of heart 90, in accordance with some applications of the invention. Particularly, leaflet support 20 is shown expanding into the expanded state as it is exposed from delivery tool 80.

Illustrating implantation of leaflet support 20 at tricuspid valve 60 is not meant to exclude implantation of leaflet support 20 at other native valves (e.g., a mitral valve 74) of heart 90, mutatis *mutandis*.

Figure 4B:
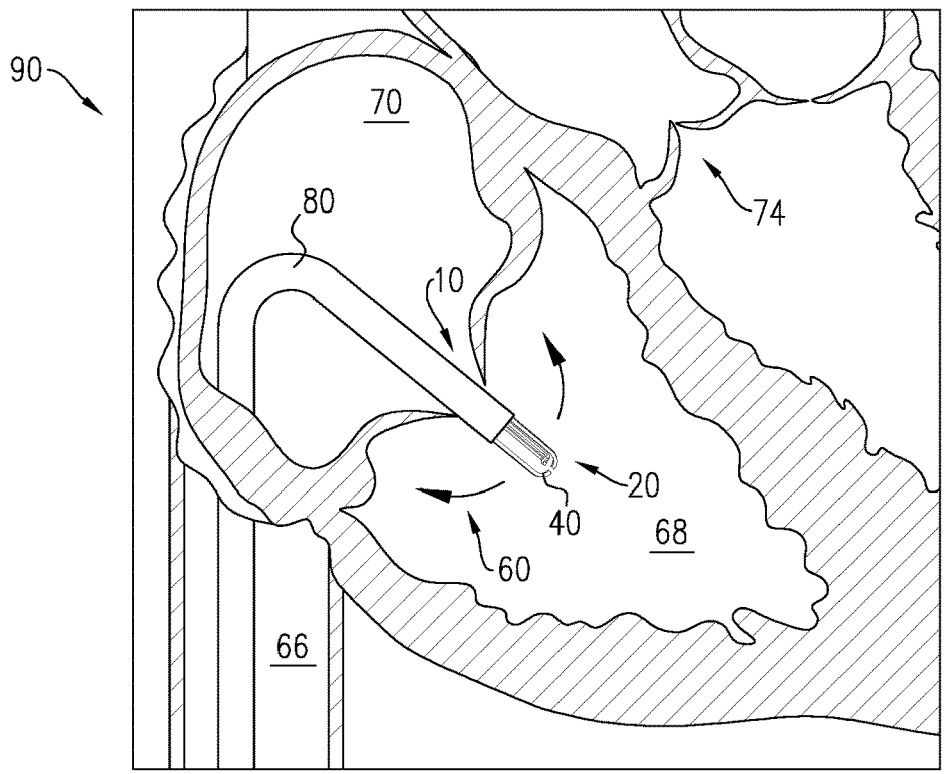
Figure 4C:
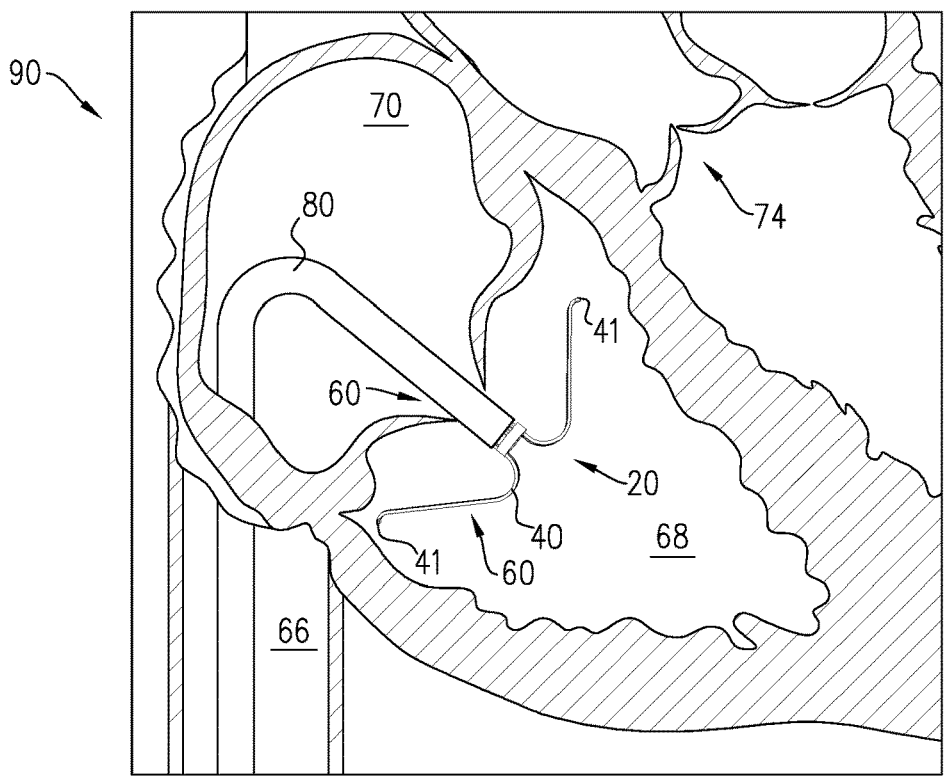

FIG. 4A shows delivery tool 80 having been advanced via inferior vena cava 66, through right atrium 70 to right ventricle 68. As shown in FIG. 4B, delivery tool 80 has begun to be retracted over leaflet support 20 such that end-portions 41 of ventricular legs 40 are exposed from the tool. FIG. 4C shows delivery tool 80 having been further retracted over leaflet support 20, such that ventricular legs 40 are further exposed from the tool. As described hereinabove, shape-memory of ventricular legs 40 causes the legs to extend radially outward.

Figure 4D:
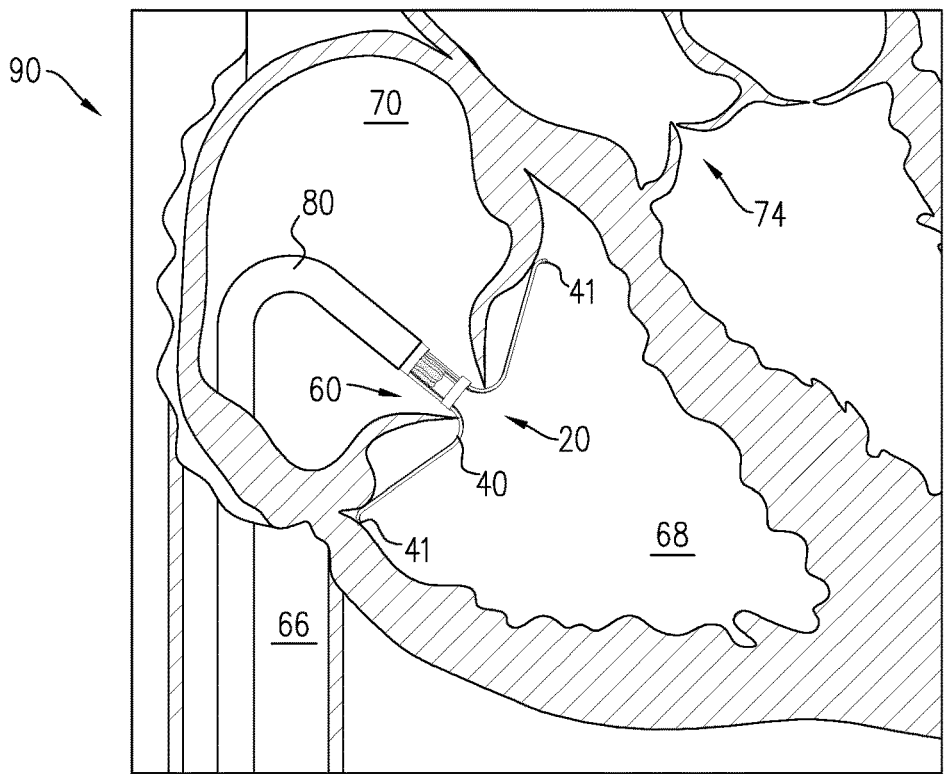
Figure 4E:
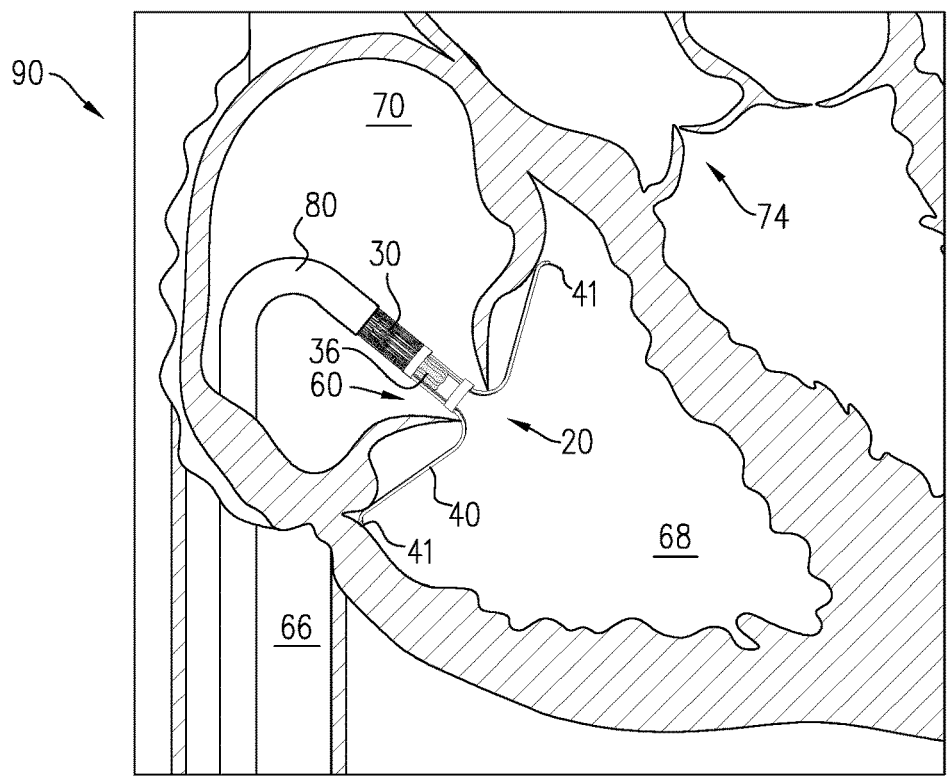
Figure 4F:
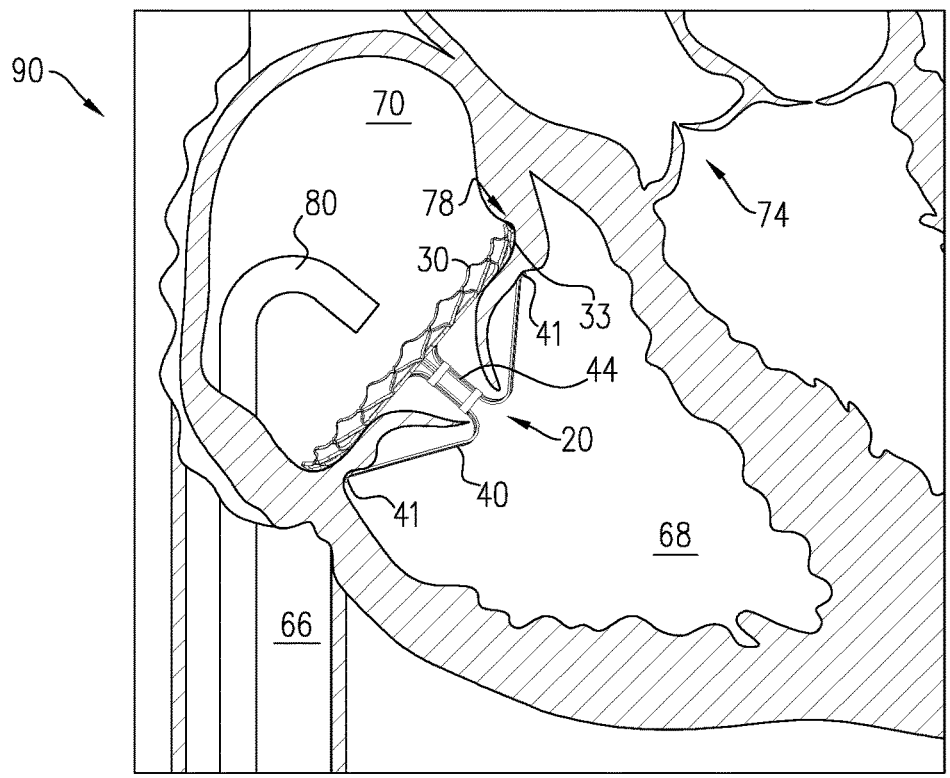

Accordingly, FIG. 4D shows ventricular legs 40 having extended further radially outward, as delivery tool 80 is further retracted, exposing connecting portion 44. Since a frame 30 is still disposed within tool 80, connecting portion 44 typically remains at least compressed, as the frame is exposed from the tool (FIG. 4E). As shown in FIG. 4F, leaflet support 20 is deployed such that frame 30 is disposed upstream of annulus 48 of tricuspid valve 60. As shown, frame 30 (e.g., annulus-fitting zone 33 thereof) is placed against annulus 48 such that tissue of the annulus supports leaflet support 20. For some applications, and as shown, while frame 30 is supported by tissue of annulus 48, ventricular legs 40 contact valvular tissue on the ventricular side of tricuspid valve 60.

Figure 5:
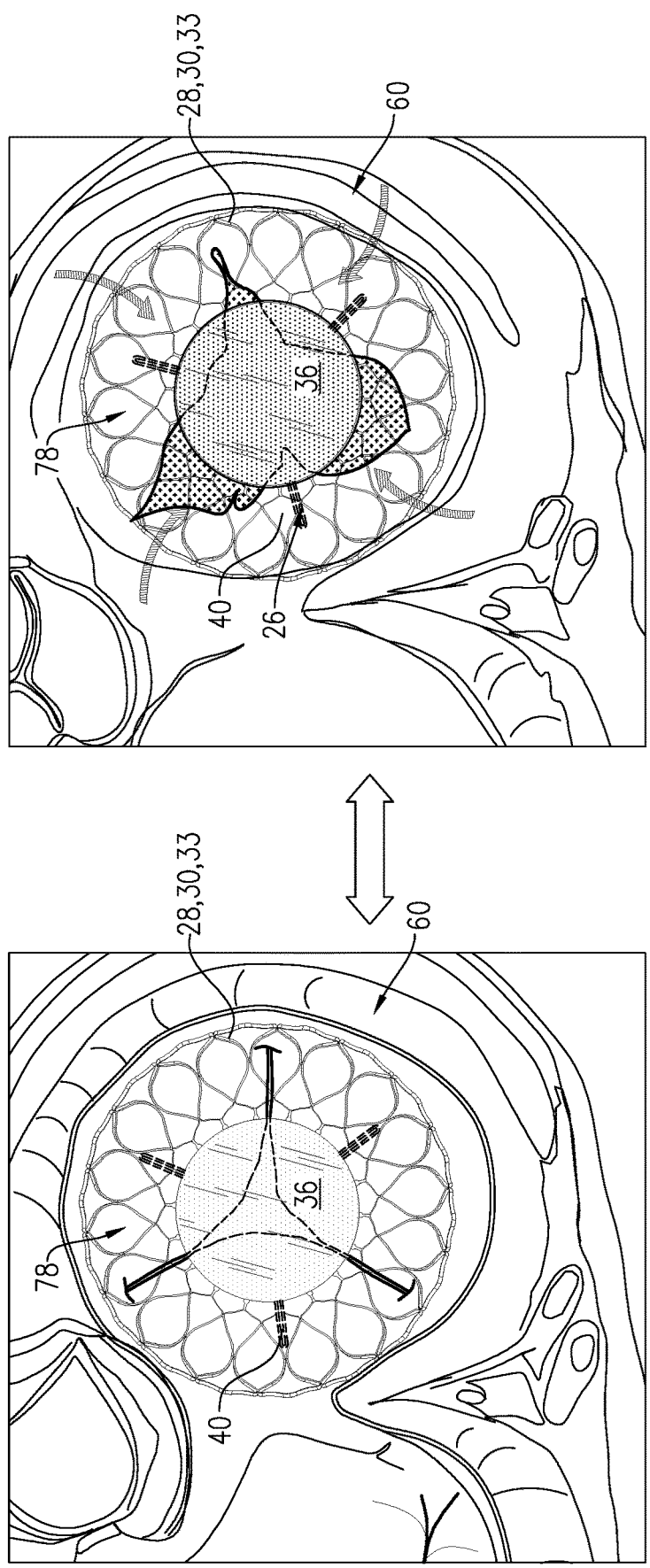
FIG. 5 includes schematic illustrations showing the leaflet support implanted at the tricuspid valve, in accordance with some applications of the present invention.

Reference is made to FIG. 5, which includes schematic illustrations showing leaflet support 20 implanted at tricuspid valve 60, in accordance with some applications of the invention. The left pane of FIG. 5 shows tricuspid valve 60 during ventricular systole, and the right pane of FIG. 5 shows the tricuspid valve during ventricular diastole.

As shown, leaflet support 20 is typically sized such that frame 30 fits annulus 48 of tricuspid valve 60 (e.g., such that frame 30 (e.g., annulus-fitting zone 33 thereof) can be placed against the annulus). For example, a greatest width (e.g., a greatest diameter) of the ring formed by frame 30 (measured transverse to a central axis d18 of support 20) may be greater than 20 mm (e.g., greater than 30 mm, e.g., greater than 40 mm, e.g., greater than 50 mm, e.g., greater than 60 mm, e.g., greater than 70 mm, e.g., greater than 80 mm, e.g., greater than 90 mm) and/or less than 100 mm (e.g., less than 90 mm, e.g., less than 80 mm, e.g., less than 70 mm, e.g., less than 60 mm, e.g., less than 50 mm, e.g., less than 40 mm, e.g., less than 30 mm). Further, a greatest width of support 20 as a whole (measured transverse to axis d18) may be greater than 20 mm (e.g., greater than 30 mm, e.g., greater than 40 mm, e.g., greater than 50 mm, e.g., greater than 60 mm, e.g., greater than 70 mm, e.g., greater than 80 mm, e.g., greater than 90 mm) and/or less than 100 mm (e.g., less than 90 mm, e.g., less than 80 mm, e.g., less than 70 mm, e.g., less than 60 mm, e.g., less than 50 mm, e.g., less than 40 mm, e.g., less than 30 mm).

It is hypothesized by the inventors that implantation of leaflet support 20 at tricuspid valve 60 may facilitate treatment of different pathological processes effecting heart 90. For example, in some cases, one or more of the native leaflets may translate or "flail" from right ventricle 68 into right atrium 70 (e.g., during ventricular systole). It is hypothesized by the inventors that upon implantation of leaflet support 20 at the native valve, barrier 36 and/or frame 30 may be disposed such that they obstruct flailing of the native leaflets. In some cases, the subject may experience retrograde blood flow, or "regurgitation" from a ventricle to an atrium of the heart (e.g., during ventricular systole). It is therefore further hypothesized by the inventors that upon implantation of leaflet support 20 at the native valve, barrier 36 obstruct regurgitation.

The right pane of FIG. 5 shows the native leaflets having deflected downstream as heart 90 cycles from ventricular systole to ventricular diastole. As shown, leaflet support 20 typically affords the native leaflets a range of motion in which to deflect during the cardiac cycle. Arrows indicate antegrade blood flow from right atrium 70 on upstream side 22 of support 20 to right ventricle 68 on downstream side 24 of the ring. Since barrier 36 typically obstructs blood flow through aperture 34, arrows indicate flow of blood via cells 32, radially outward of the barrier.

Figure 6A:
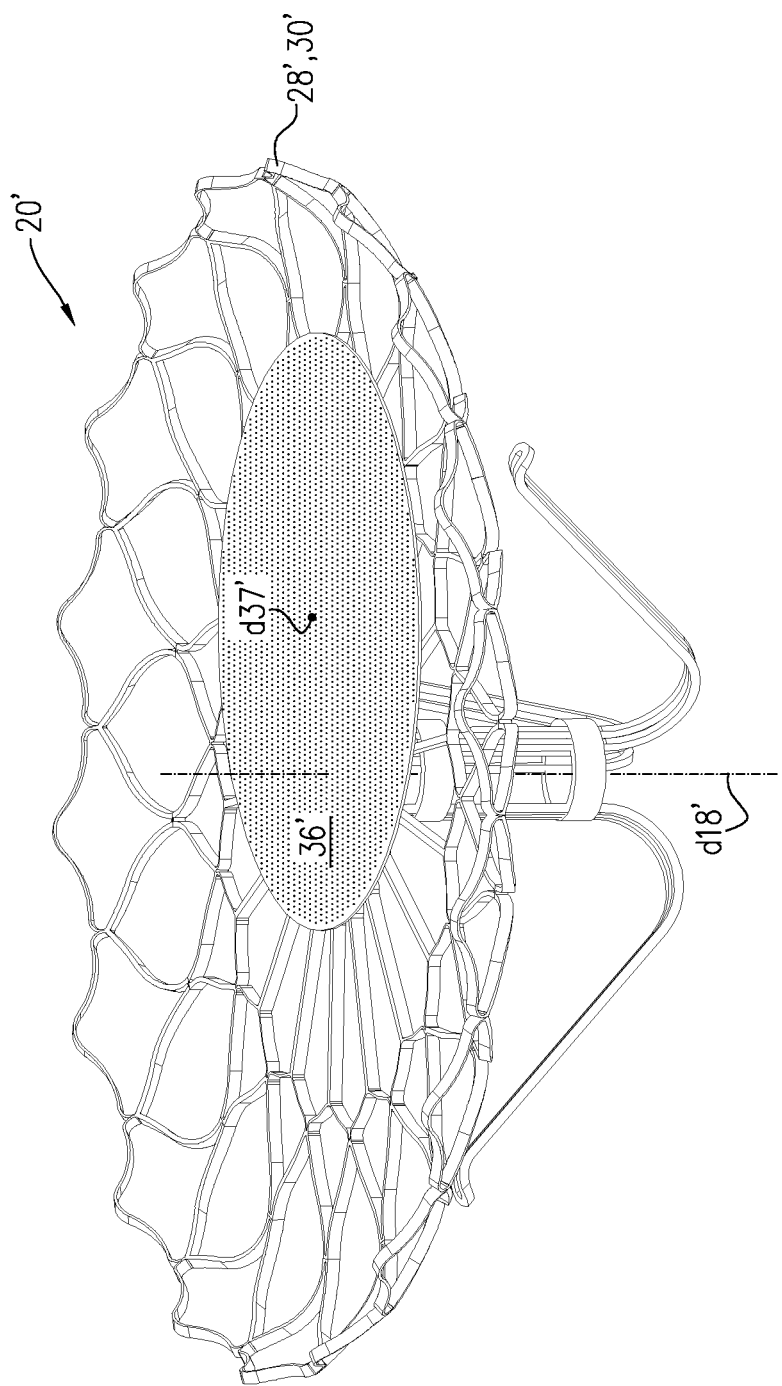
FIGS. 6A-B are schematic illustrations showing a leaflet support, in accordance with some applications of the present invention.
Figure 6B:
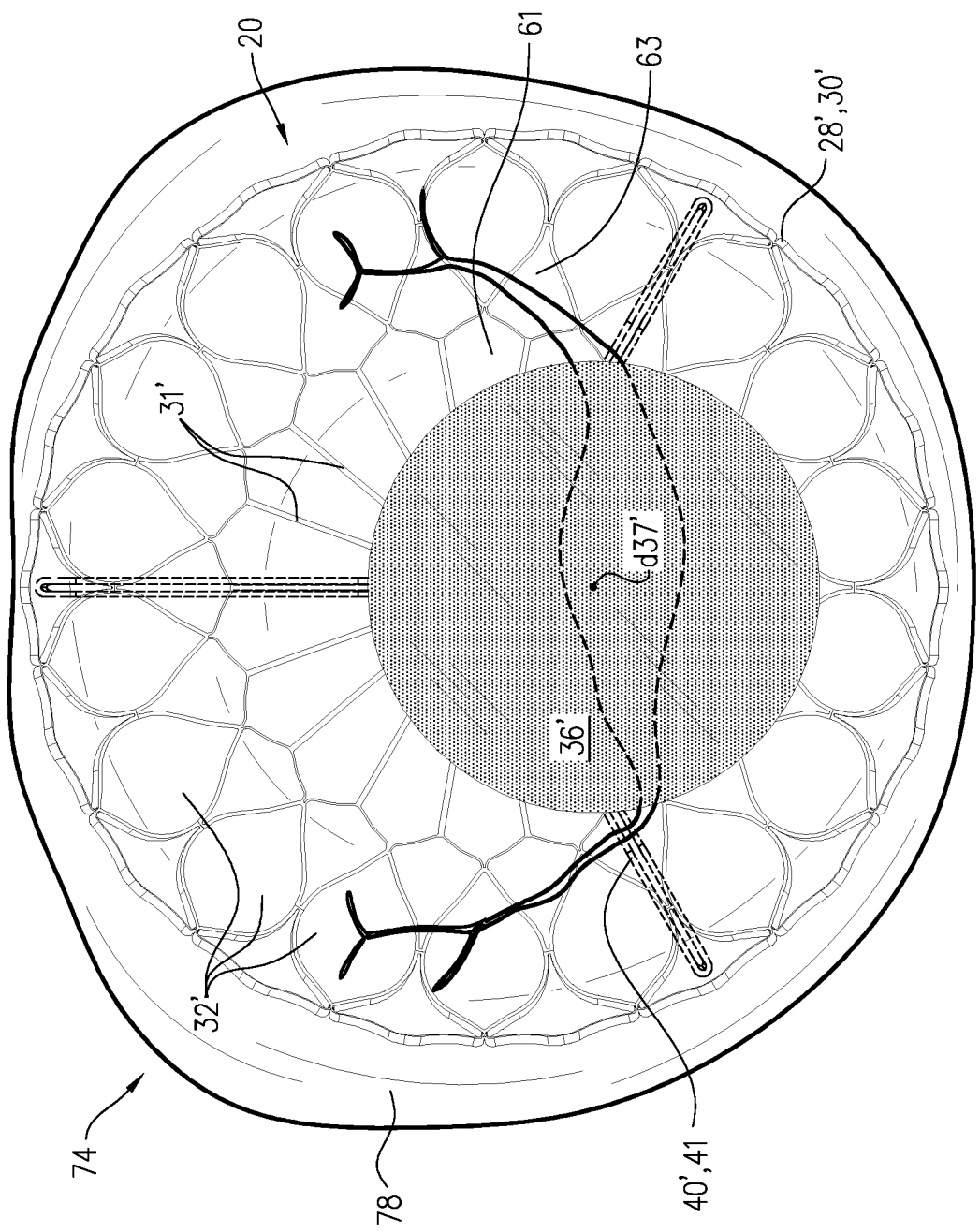

Reference is made to FIGS. 6A-B, which are schematic illustrations showing a leaflet support 20', in accordance with some applications of the invention.

As shown, leaflet support 20' is generally similar to leaflet support 20. Accordingly, components bearing identical reference numerals are typically interchangeable between leaflet support 20' and leaflet support 20.

Leaflet support 20' comprises a ring-shaped frame 30' that defines an array of adjoining cells 32'. Frame 30' is typically similar to frame 30, except where noted. Leaflet support 20' further comprises a barrier 36' that is impermeable to blood flow. Barrier 36' is typically similar to barrier 36, except where noted.

One difference between leaflet support 20' and leaflet support 20 lies in that barrier 36' is offset with respect to frame 30' (e.g., with respect to an outer ring-perimeter 28' of the frame). That is, a central axis d18' of support 20' does not pass through a center point d37' of barrier 36'. For some applications, and as shown in FIG. 6A, central axis d18' nonetheless passes through barrier 36'.

For some applications, and as shown, barrier 36 covers a portion of frame 30 (e.g., at least a portion of at least one cell 32'), such that the barrier obstructs blood flow through the portion of the frame. For some such applications, and as shown, barrier 36' is coupled to frame 30' via a plurality of ring struts 31' that extend from at least some of cells 32'. In this way, barrier 36' is disposed off-center with respect to frame 30'. Alternatively or in addition, the shape or number of cells 32' defining frame 30' may be altered, relative to frame 30, thereby facilitating coupling barrier 36' off of center with respect to frame 30'.

It is hypothesized by the inventors that the offset barrier 36' of leaflet support 20' may advantageously fit certain native valves (e.g., mitral valve 74, as shown). That is, in some cases, a site of leaflet flailing and/or regurgitation may be offset with respect to annulus 48 of the native valve. Therefore, in some such cases, offset leaflet support 20' may be advantageously implanted at the native valve, such that barrier 36' will be favorably positioned to block the flailing and/or regurgitation. For example, it may be desirable for two legs 40' to be disposed radially closer to each other than they are to a third leg, as described hereinabove in reference to FIGS. 1A-C, in order to facilitate positioning barrier 36 favorably for blocking the flailing and/or regurgitation.

FIG. 6 showing support 20' implanted at mitral valve 74 is not intended to exclude cases in which non-offset leaflet support 20 may be advantageously implanted at mitral valve 74, or wherein offset leaflet support 20' may be advantageously implanted at tricuspid valve 60.

Reference is made to FIGS. 7A-F, which are schematic illustrations showing use of a system 110 comprising a barrier-delivery tool 150 and a leaflet support 120, in accordance with some applications of the invention.

As shown, leaflet support 120 is generally similar to leaflet support 20'. Accordingly, components bearing identical reference numerals are typically interchangeable between leaflet support 120 and leaflet support 20'.

For some applications, and as shown, a barrier-delivery tool 150 may be used to couple a barrier 136 to frame 130 of support 120. For some such applications, and as shown in FIG. 7A, delivery tool 150 is also used to deploy frame 130 of support 120 at the native valve. For example, and as shown, delivery tool 150 may reversibly connect to a portion of frame 130. It is hypothesized by the inventors that delivery tool 150 being reversibly connected to frame 130 facilitates use of the delivery tool to couple barrier 136 to the frame, as described hereinbelow.

A difference between supports 120 and 20' is that while support 20' is typically provided with barrier 36' already coupled to frame 30', for some applications and as shown in FIG. 7A, frame 130 is deployed at the heart prior to coupling barrier 136 to the frame. Typically for such applications, barrier 136 is transluminally advanced to the heart before the barrier is coupled to frame 130. That is, barrier 136 may be coupled to frame 130 during deployment of the leaflet support 120.

For some applications, and as shown, barrier 136 is transluminally coupled to frame 130 after the frame is implanted at the native valve (e.g., while the frame remains disposed at the native valve).

FIG. 7B shows barrier 136 being deployed from a barrier-delivery capsule 154 of barrier-delivery tool 150. For some applications, and as shown in the inset of FIG. 7C, barrier 136 comprises a flexible sheet (e.g., a fabric sheet) 138 that is coupled to a barrier-frame 135. For example, and as shown, barrier-frame 135 may be ring-shaped. Alternatively or in addition, barrier-frame 135 may be shaped to define cells, and/or radially-aligned elements. For some such applications, barrier-frame 135 comprises a shape-memory material. For some such applications, barrier 136 is constrained within barrier-delivery capsule 154 to a compressed width (e.g., a compressed diameter), and exposure of the barrier from capsule 154 causes the barrier to expand to an expanded width (e.g., an expanded diameter). In this way, expansion of the barrier to the expanded width typically causes sheet 138 to cover barrier-frame 135 such that the sheet obstructs blood flow through the barrier-frame.

FIG. 7C shows barrier 136 having been deployed from barrier-delivery capsule 154, at an intermediate step in which barrier 136 is still engaged by delivery tool 150. During this intermediate step, extracorporeal control of delivery tool 150 regulates both: (i) longitudinal movement of barrier 136 along a central axis d116 of barrier-delivery tool 150, and (ii) rotation of the barrier about the central axis. In this way, delivery tool 150 facilitates alignment of barrier 136 to a desired portion of frame 130.

FIG. 7D shows barrier 136 having been rotated about central axis d116 of delivery tool 150. For some applications, and as shown, barrier 136 is offset with respect to tool 150. That is, central axis d116 of tool 150 does not pass through a center-point d137 of barrier 136.

For some applications, and as shown, barrier 136 comprises a frame-fitting portion 152 that is dimensioned to fit (e.g., to snugly engage) a portion of frame 130. For some applications, barrier 136 is offset with respect to frame-fitting portion 152 thereof. That is, frame-fitting portion 152 is defined at a portion of barrier 136 that is radially outward of center-point d137. In this way, and as shown, rotation of barrier 136 about frame-fitting portion 152 positions a greater portion of the barrier on a particular side of the frame-fitting portion.

For some applications, and as shown, central axis d116 and a central axis d118 of support 120 are coaxial, such that rotation of barrier 136 using delivery tool 150 also rotates the barrier with respect to frame 130. In this way, rotation of barrier 136 may be used to align the barrier with a desired portion of frame 130, prior to coupling the barrier to the frame, which is hypothesized by the inventors to facilitate alignment of the barrier with a desired anatomical location (a location identified with leaflet flailing and/or regurgitation) of the native valve.

As shown in FIGS. 7D-E, barrier 136 is typically coupled to frame 130, after the barrier is radially aligned to the desired portion of the barrier, e.g., by fitting frame-fitting portion 152 to frame 130. For some applications, and similarly to barrier 36', barrier 136 is offset with respect to frame 130. Typically, and as shown in FIG. 7F, after barrier 136 is coupled to frame 130, the barrier is decoupled from delivery tool 150. Delivery tool 150 is removed from the subject, such that fully assembled support 120 remains at the native valve.

Figure 8C:
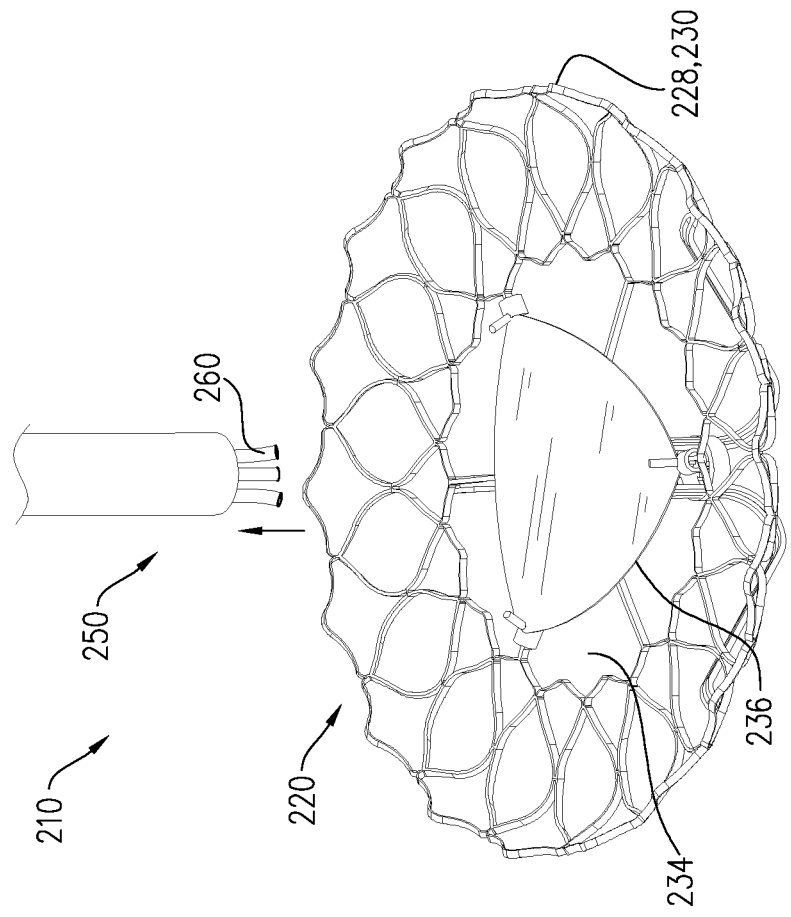
Figure 8B:
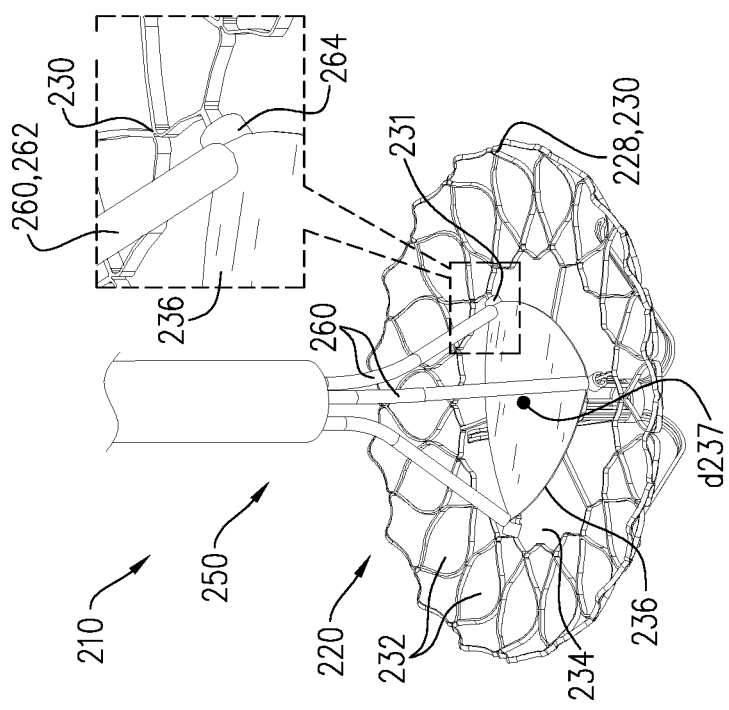

Reference is made to FIGS. 8A-C, which are schematic illustrations showing a system 210 comprising a leaflet support 220 and an adjustment tool 250, in accordance with some applications of the invention.

As shown, leaflet support 220 is generally similar to leaflet support 20. Accordingly, components bearing identical reference numerals are typically interchangeable between leaflet support 220 and leaflet support 20.

Leaflet support 220 comprises a ring-shaped frame 230 that defines an array of adjoining cells 232, and that is typically similar to frame 30, except where noted. Leaflet support 220 further comprises a barrier 236 (e.g., comprising a flexible sheet) that is impermeable to blood flow.

A difference between supports 20 and 220 is that whereas barrier 36 is typically fixedly coupled to frame 30, barrier 236 is adjustably coupled to frame 230 (e.g., to one or more sizing struts 231 thereof). Typically, and as shown, barrier 236 is transluminally adjustable in a manner that adjusts a portion of an area of aperture 234 (an "aperture area") that is covered by the barrier. For example, the portion of the aperture area covered by barrier 236 may be repositioned and/or resized.

For some applications, and as shown, an adjustment tool 250 may be used to transluminally adjust the portion of the aperture area covered by barrier 236. For some such applications, adjustment tool 250 also facilitates implantation of support 220 at the native valve (e.g., may be a component of a delivery tool).

For some applications, barrier 236 comprises one or more adjustment locks 264 configured to facilitate engagement of the barrier by tool 250. FIG. 8A shows support 220 having been implanted at the native valve, and adjustment tool 250 engaging adjustment locks 264 of barrier 236. For some applications, and as shown, each end-portion 262 of a respective arm 260 of adjustment tool 250, engages an adjustment lock 264 of barrier 236.

For some applications, adjustment tool 250 is extracorporeally controlled to transfer a force to barrier 236 (e.g., to adjustment locks 264 thereof) in order to change the portion of the aperture area covered by the barrier. As shown in FIG. 8B, the force has caused adjustment lock 264 to move along sizing strut 231, radially away from center-point d237 of barrier 236 and toward outer ring-perimeter 228.

In response to radial movement of adjustment lock 264, barrier 236 may stretch and/or move, thereby adjusting the portion of the aperture area covered by the barrier. For some applications, barrier 236 comprises an elastic material. Therefore, for some such applications, radial movement of adjustment lock 264 stretches barrier 236 such that a greater portion of the aperture area becomes covered by the barrier. Alternatively, barrier 236 may comprise a nonelastic material that is incapable of stretching in response to radial movement of adjustment lock 264. Therefore, for some such applications, radial movement of one of the adjustment locks 264 causes movement of barrier 236 (e.g., such that the entire barrier moves radially). Alternatively still, barrier 236 may comprise a slightly elastic material, such that radial movement of adjustment lock 264 both stretches and causes movement of the barrier.

It is generally desirable that the change in the portion of the aperture area covered by barrier 236 remain in effect, after adjustment tool 250 has been disengaged and removed. Therefore, support 220 typically comprises a locking mechanism to retain barrier 236 in its adjusted configuration. For example, and as shown, frame 230 may comprise sizing struts 231 (inset of FIG. 8A). For some such applications, sizing struts 231 are shaped to define angled protrusions 235 along a length of the sizing struts. For example, the protrusions may be shaped such that a greater force is required to move adjustment lock 264 radially outward along sizing strut 231, than is required to move the lock radially inward along the sizing strut. In this way, adjustment lock 264 may be anticipated to remain in the radial position to which the lock was advanced by adjustment tool 250, also after disengagement of the tool from the lock. As such, the portion of the aperture area covered by barrier 236 while tool 250 engages the barrier may be anticipated to be maintained, after disengagement of the tool from the barrier.

FIG. 8C shows adjustment tool 250 having been transluminally withdrawn, such that the position of adjustment lock 264, as well as the portion of the aperture area covered by barrier 236, remains generally similar to that shown in FIG. 8B.

In FIGS. 8A-C, barrier 236 is shown as being generally triangular in shape (e.g., a circular triangle, such as a Reuleaux triangle or a deltoid curve). While it is hypothesized by the inventors that such a triangular shape may facilitate stretching barrier 236 towards one or more corners of the barrier (e.g., for use with an adjustment tool 250 that comprises three arms 260), other shapes of the barrier, and corresponding configurations of adjustment tool 250, mutatis *mutandis*, are contemplated.

Figure 9:
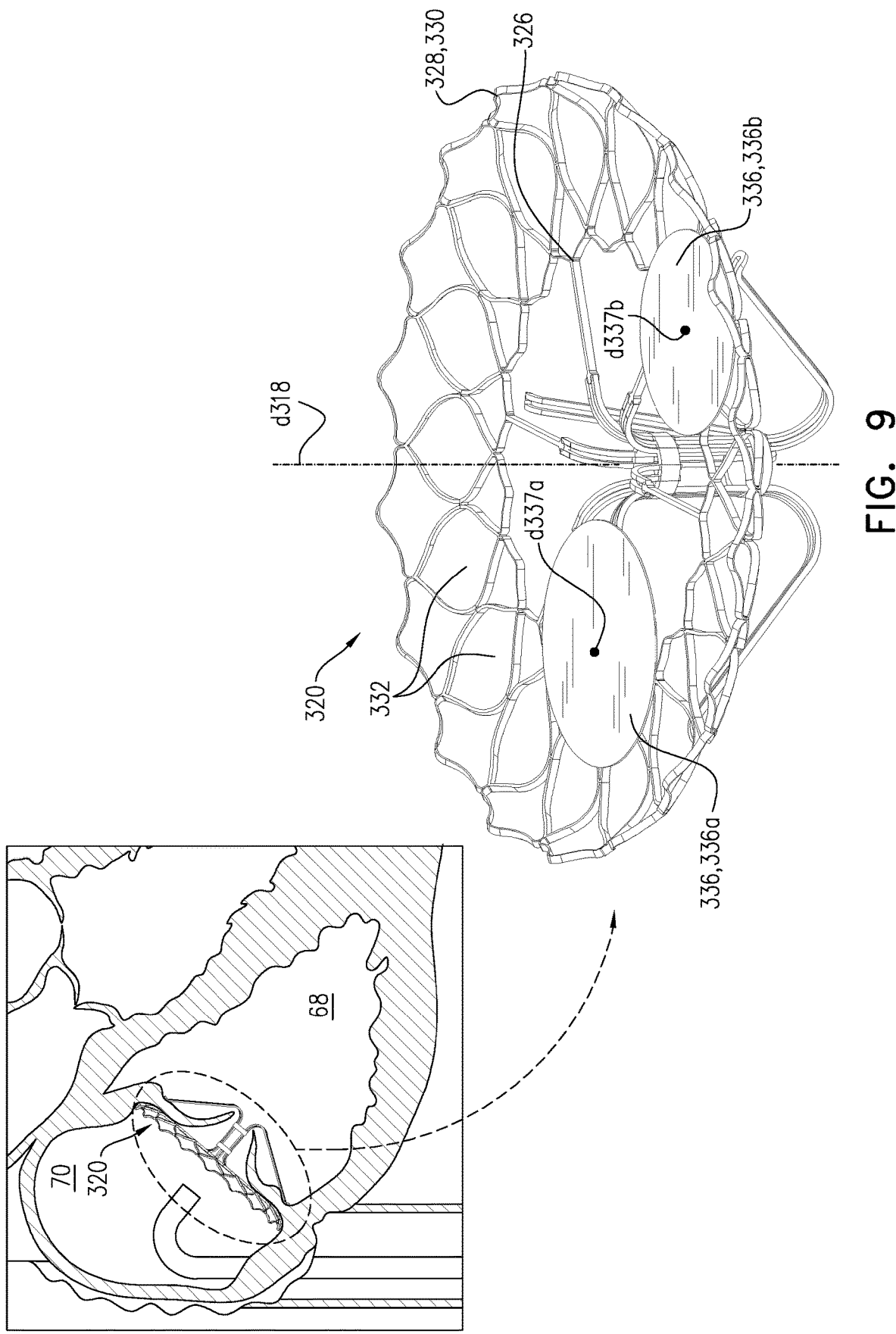
FIG. 9 is a schematic illustration showing a leaflet support, in accordance with some applications of the invention.

Reference is made to FIG. 9, which is a schematic illustration showing a leaflet support 320, in accordance with some applications of the invention.

As shown, leaflet support 320 is generally similar to leaflet support 20. Accordingly, components bearing identical reference numerals are typically interchangeable between leaflet support 320 and leaflet support 20.

Leaflet support 320 comprises a ring-shaped frame 330 that defines an array of adjoining cells 332. Similarly to frame 30, frame 330 extends radially outward from an aperture 334 that is defined by an inner ring-perimeter 326, to an outer ring-perimeter 328.

Further similarly to leaflet support 20, support 320 comprises a blood flow-impermeable barrier 336 that is coupled to frame 330 such that the barrier obstructs blood flow through aperture 334. However, a difference between supports 20 and 320 is that support 320 comprises a plurality of barriers 336 (e.g., two barriers, such as 336a and 336b shown in FIG. 9, or more). For some applications, each of barriers 336 obstructs blood flow not only through aperture 334, but also through a portion of frame 330. However, barriers 336 are typically spaced apart from each other to allow blood flow between the respective barriers and through frame 330.

For some applications, barriers 336 are offset with respect to frame 330. That is, a central axis d318 does not pass through respective center-points d337a or d337b of barriers 336a, 336b. For some such applications, and as shown, central axis d318 does not pass through any portion of barriers 336a, 336b.

For some applications, support 320 is provided with barriers 336 fixedly coupled to frame 330—i.e., the position of the barriers is predetermined. Alternatively, the position of one or more of barriers 336 may be adjusted (e.g., relative to aperture 334 and frame 330), e.g., according to the judgement of a clinician. For example, the respective positions of barriers 336 may be adjusted prior to delivery of support 320 to the heart, and/or after fastening frame 330 to the native valve (e.g., transluminally, as described hereinabove in reference to FIGS. 8A-B).

Reference is made to FIGS. 10A-C, which are schematic illustrations showing perspective views of a leaflet support 420, a leaflet support 520 and a leaflet support 620, in accordance with some applications of the invention.

Certain aspects of leaflet supports 420, 520, 620 are shared with previously described leaflet support 20. Thus, components that are identically named between supports 420, 520, 620 and support 20 share similar features and serve similar functions as each other. Similarly to support 20, supports 420, 520, 620 comprise a frame 430, 530, 630 that defines an aperture 434, 534, 634, as well as ventricular legs 440, 540, 640 and a barrier 436, 536, 636. Similarly to frame 30 of leaflet support 20 described hereinabove, frame 430, 530, 630 defines an array of adjoining cells 432, 532, 632 that form a ring that extends radially outward from an inner ring-perimeter 426, 526, 626 to an outer ring-perimeter 428, 528, 628. Further similarly to frame 30 of support 20, frame 430, 530, 630 is configured to facilitate blood flow between an upstream side 422, 522, 622 and a downstream side 424, 524, 624 of respective rings formed by each support 420, 520, 620.

Further similarly to barrier 36 of leaflet support 20, barrier 436, 536, 636 of support 420, 520, 620 obstructs blood flow through aperture 434, 534, 634. However, in contrast to leaflet support 20, leaflet support 420, 520, 620 comprises a tubular portion 442, 542, 642 that supports the barrier. As shown, tubular portion 442, 542, 642 comprises a circumferential wall 446, 546, 646 that extends between an upstream end 445 and a downstream end 447 of the tubular portion.

For some applications, a circumferential space 448, 548, 648 (e.g., that circumscribes circumferential wall 446, 546, 646) is defined between tubular portion 442, 542, 642 and legs 440, 540, 640. Typically for such applications, circumferential space 448, 548, 648 is both: (i) radially inward from legs 440, 540, 640, and (ii) downstream of a downstream side 424, 524, 624 of frame 430, 530, 630. In this way, circumferential space 448, 548, 648 is typically free of elements that would obstruct movement of leaflets of the native valve. It is hypothesized by the inventors that circumferential space 448, 548, 648 facilitates functioning of the native valve while leaflet support 420, 520, 620 is implanted at that valve, by allowing leaflets of the native valve to deflect as heart 90 cycles between ventricular systole and ventricular diastole.

Typically for applications in which the leaflet support comprises a tubular portion, the tubular portion is positioned and sized to facilitate obstruction of blood flow through aperture, as described hereinbelow.

For some applications, and as shown, tubular portion 442, 542, 642 is coupled to frame 430, 530, 630 downstream of aperture 434, 534, 634 (e.g., the tubular portion is connected to inner ring-perimeter 426, 526, 626).

For some applications, tubular portion 442, 542, 642 and aperture 434, 534, 634 are of similar width (e.g., such that a tubular area is no less than 80 percent of an aperture area, and up to 120 percent of the aperture area). For some such applications, the tubular area is equal to the aperture area.

For some applications, and as shown in FIG. 10A, tubular portion 442, 542, 642 is radially centered with respect to frame 430, 530, 630. That is, circumferential wall 446, 546, 646 circumscribes central axis d418, d518, d618 of leaflet support 20.

For some applications, leaflet support 420, 520, 620 is configured to obstruct blood flow not just through aperture 434, 534, 634 but also through tubular portion 442, 542, 642.

For some such applications, and as shown, a circumferential sleeve 449, 549, 649 is coupled to (e.g., covers) circumferential wall 446, 546, 646. Circumferential sleeve 449, 549, 649 is typically impermeable to blood flow (e.g., the sleeve may comprise the same material as the barrier). It is hypothesized by the inventors that implanting support 420, 520, 620 at the native valve may advantageously mitigate regurgitation by circumferential sleeve 449 acting as a spacer against which the native leaflets may coapt against during ventricular systole.

For some such applications, and as shown regarding support 420, barrier 436 (e.g., barrier 436a and barrier 436b) covers both upstream end 445 (FIG. 10B) and downstream end 447 (FIG. 10C) of tubular portion 442.

Figure 12:
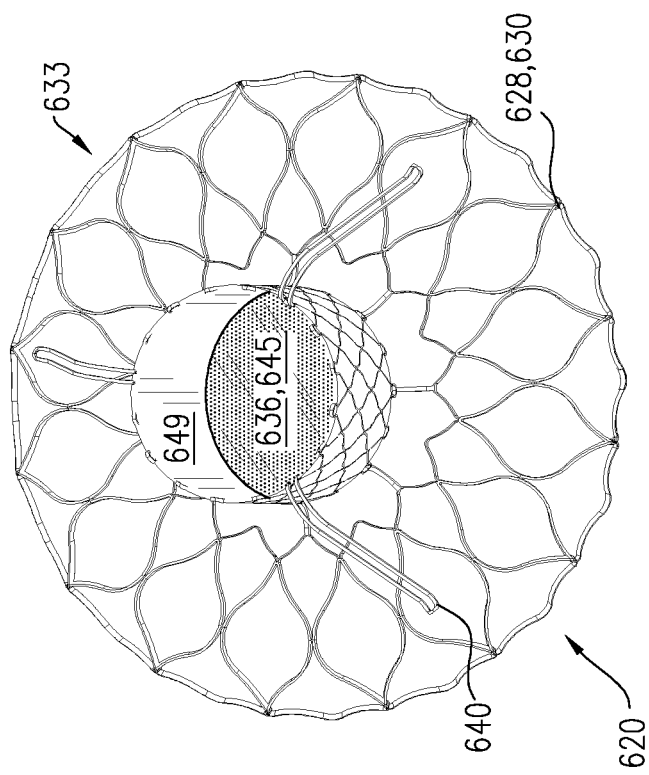
FIGS. 11-12 are schematic illustrations showing perspective views of certain leaflet supports, in accordance with some applications of the present invention.
Figure 11:
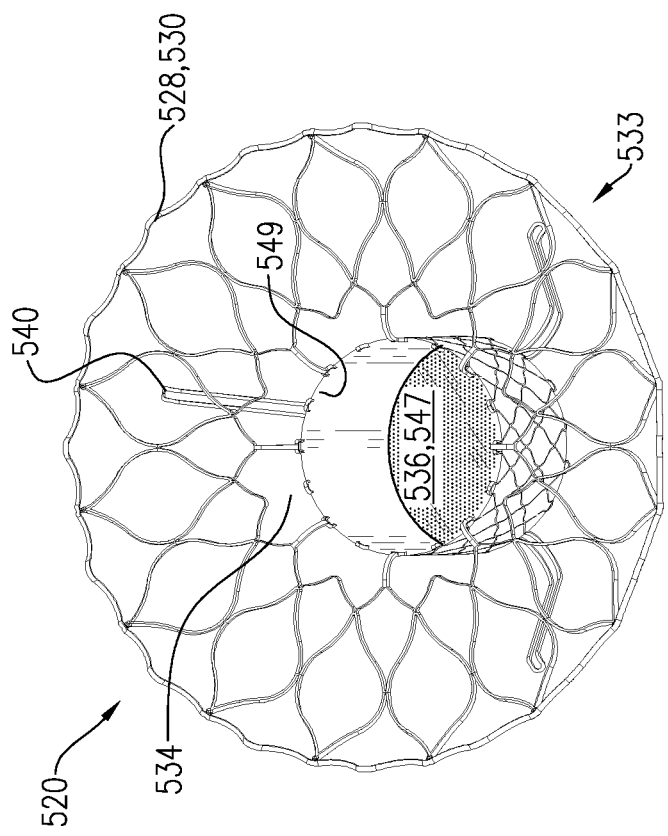

Reference is made to FIGS. 11-12, which are schematic illustrations showing perspective views of leaflet supports 520, 620, in accordance with some applications of the invention.

As shown, and in contrast to support 420, supports 520 and 620 each have an open end, not covered by respective barrier 536, 636. That is, tubular portion 542 of support 520 has an open upstream end (FIG. 11), while barrier 536 covers downstream end 547 (FIG. 10C). Complementarily, tubular portion 642 of support 620 has an open downstream end (FIG. 12), while barrier 636 covers upstream end 645 (FIG. 10B).

When considering supports 420, 520, 620 in relation to support 20, tubular portion 442, 542, 642 may be considered to serve as a connecting portion (e.g., similar to connecting portion 44, mutatis *mutandis*). That is, tubular portion 442, 542, 642 couples ventricular legs 440, 540, 640 to frame 430, 530, 630, while also coupling the legs to each other.

Therefore, another difference between supports 420, 520, 620 and support 20 lies in the respective point from which each leg 440, 540, 640 extends radially outward and upstream, toward frame 430, 530, 630. That is, for some applications, each leg 440, 540, 640 extends outward and upstream from tubular portion 442, 542, 642. For some such applications, each leg 440, 540, 640 extends further outward than barrier 436, 536, 636 and/or inner ring-perimeter 426, 526, 626.

In other respects, supports 420, 520, 620 are similar to support 20 described hereinabove. For some applications, and similarly to central axis d48 of support 20, central axis d418, d518, d618 passes through barrier 436, 536, 636 (e.g., such that the central axis passes through a center point of the barrier). Alternatively or in addition, central axis d418, d518, d618 may pass through aperture 434, 534, 634 (e.g., such that central axis d418 passes through a center point of the aperture).

Supports 420, 520, 620 are typically sized to fit annulus 48 of the native valve. For example, a greatest width (e.g., a greatest diameter) of the ring formed by frame 430, 530, 630 (measured transverse to a central axis d418, d518, d618 of support 420, 520, 620) may be greater than 20 mm (e.g., greater than 30 mm, e.g., greater than 40 mm, e.g., greater than 50 mm, e.g., greater than 60 mm, e.g., greater than 70 mm, e.g., greater than 80 mm, e.g., greater than 90 mm) and/or less than 100 mm (e.g., less than 90 mm, e.g., less than 80 mm, e.g., less than 70 mm, e.g., less than 60 mm, e.g., less than 50 mm, e.g., less than 40 mm, e.g., less than 30 mm). Further, a greatest width of support 420, 520, 620 as a whole (measured transverse to axis d418, d518, d618) may be greater than 20 mm (e.g., greater than 30 mm, e.g., greater than 40 mm, e.g., greater than 50 mm, e.g., greater than 60 mm, e.g., greater than 70 mm, e.g., greater than 80 mm, e.g., greater than 90 mm) and/or less than 100 mm (e.g., less than 90 mm, e.g., less than 80 mm, e.g., less than 70 mm, e.g., less than 60 mm, e.g., less than 50 mm, e.g., less than 40 mm, e.g., less than 30 mm). For some applications, and similarly to annulus-fitting zone 33, an annulus-fitting zone 433, 533, 633 of leaflet support 20 is concavely shaped (e.g., frustoconical shaped or shaped as a spherical segment).

Figure 13:
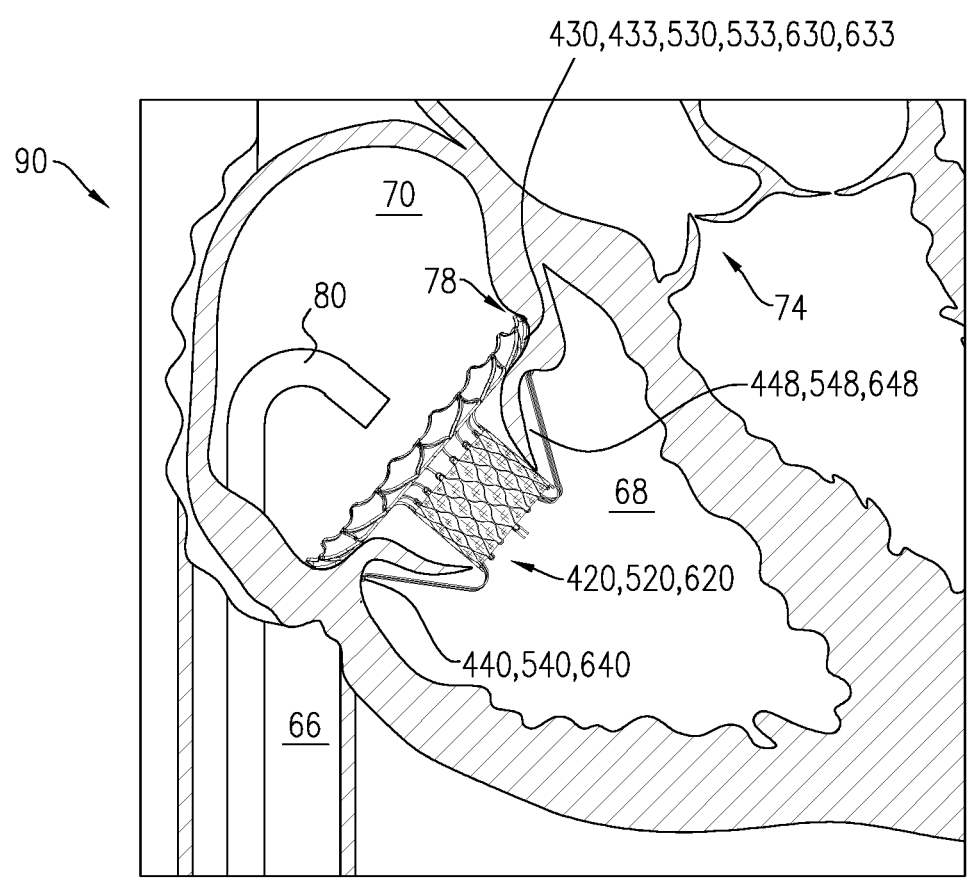

Reference is made to FIGS. 13-14, which are schematic illustrations showing leaflet support 420, 520, 620 implanted at tricuspid valve 60, in accordance with some applications of the invention.

As shown in FIG. 13, support 420, 520, 620 is deployed such that frame 430, 530, 630 is disposed upstream of annulus 48 of tricuspid valve 60. As shown, frame 430, 530, 630 (e.g., annulus-fitting zone 433, 533, 633 thereof) is placed against annulus 48 such that tissue of the annulus supports leaflet support 420, 520, 620. For some applications, and as shown, while frame 430, 530, 630 is supported by tissue of annulus 48, ventricular legs 440, 540, 640 contact valvular tissue on the ventricular side of tricuspid valve 60.

The left pane of FIG. 14 shows tricuspid valve 60 during ventricular systole, and the right pane of FIG. 14 shows the tricuspid valve during ventricular diastole. It is hypothesized by the inventors that implantation of leaflet support 20 at tricuspid valve 60 may facilitate treatment of different pathological processes effecting heart 90. For example, in some cases, one or more of the native leaflets may flail or blood may regurgitate from right ventricle 68 into right atrium 70 (e.g., during ventricular systole). It is hypothesized by the inventors that upon implantation of support 420, 520, 620 at the native valve, barrier 436, 536, 636 and/or frame 430, 530, 630 may obstruct flailing and/or regurgitation.

The right pane of FIG. 14 shows the native leaflets having deflected downstream as heart 90 cycles from ventricular systole to ventricular diastole. As shown, support 420, 520, 620 typically affords the native leaflets a range of motion in which to deflect during the cardiac cycle. Arrows indicate antegrade blood flow from right atrium 70 on upstream side 422, 522, 622 of the ring, via cells 432, 532, 632.

Figure 15B:
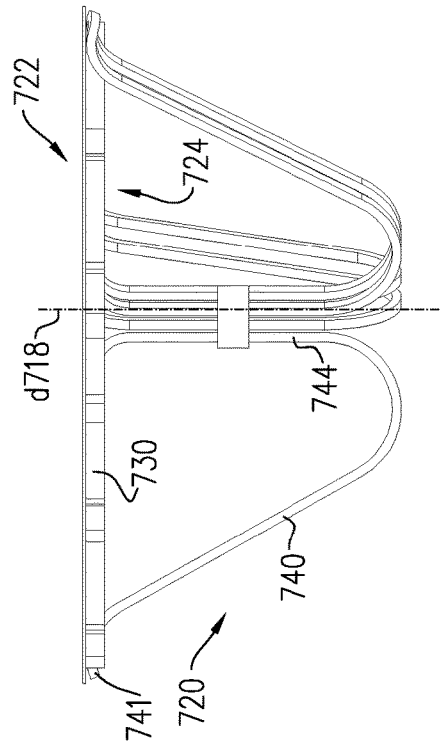
FIGS. 15A-C are schematic illustrations showing different perspective views of a leaflet support, in accordance with some applications of the present invention.
Figure 15C:
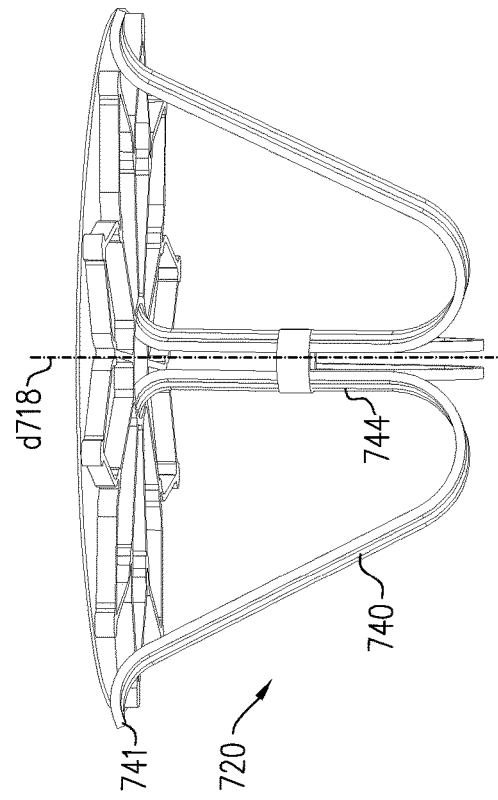
Figure 15A:
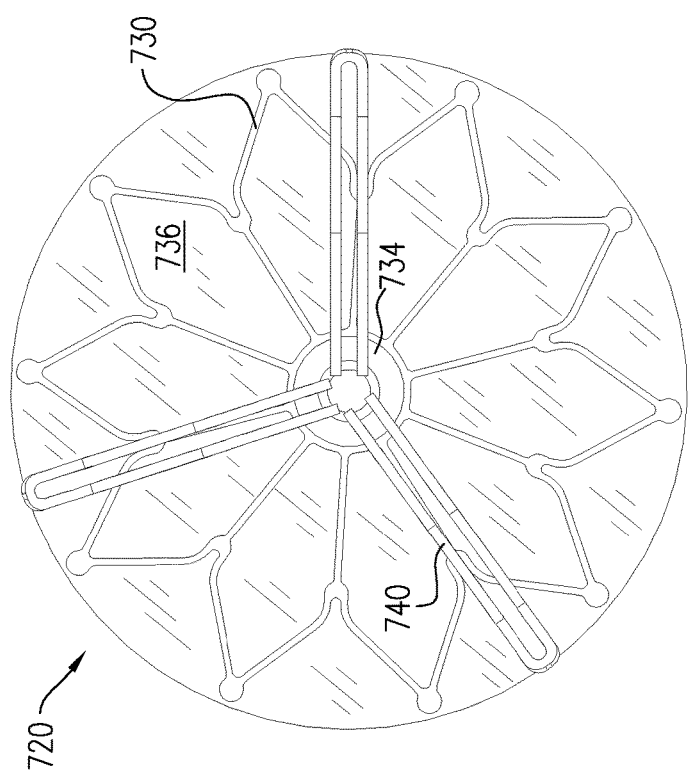

Reference is made to FIGS. 15A-C, which are schematic illustrations showing different perspective views of a leaflet support 720, in accordance with some applications of the invention.

As shown, leaflet support 720 is in many ways similar to leaflet support 20. Accordingly, components that are identically named between leaflet support 720 and previously described leaflet support 20 typically share similar features and serve similar functions as each other. That is, leaflet support 720 comprises a blood-impermeable barrier 736 that is coupled to a frame 730 in a manner that obstructs blood flow through an aperture 734, between an upstream side 722 and a downstream side 724 of the frame.

Further similarly to as described hereinabove with reference to FIG. 16 regarding connecting portion 44 of support 20, connecting portion 744 of leaflet support 720 connects each of a plurality of ventricular legs 740 to frame 730, such that each leg extends radially outward from the connecting portion, and upstream toward the frame. However, legs 740 of support 720 may extend further upstream than do legs 40 of support 20. For example, shape-memory of legs 740 of support 720 may be such that each leg end-portion 741 reaches (e.g., presses against) frame 730 and/or barrier 736. For some applications, leg end-portion 741 extends upstream of at least a portion of frame 730, e.g., pressing against barrier 736 such that the barrier bulges away from upstream side 722.

Another difference between leaflet support 720 and leaflet support 20 lies in the radial position of leg end-portions 41, 741 with respect to barrier 36, 736. As shown in FIGS. 1A-B, leg end-portions 41 typically extend radially outward of barrier 36. However, for some applications, and as shown, barrier 736 and legs 740 extend outward to approximately the same extent (e.g., to exactly the same extent). For some such applications, barrier 736 extends further outward than do legs 740. For some such applications, legs 740 extend further outward than does barrier 736.

Figure 16:
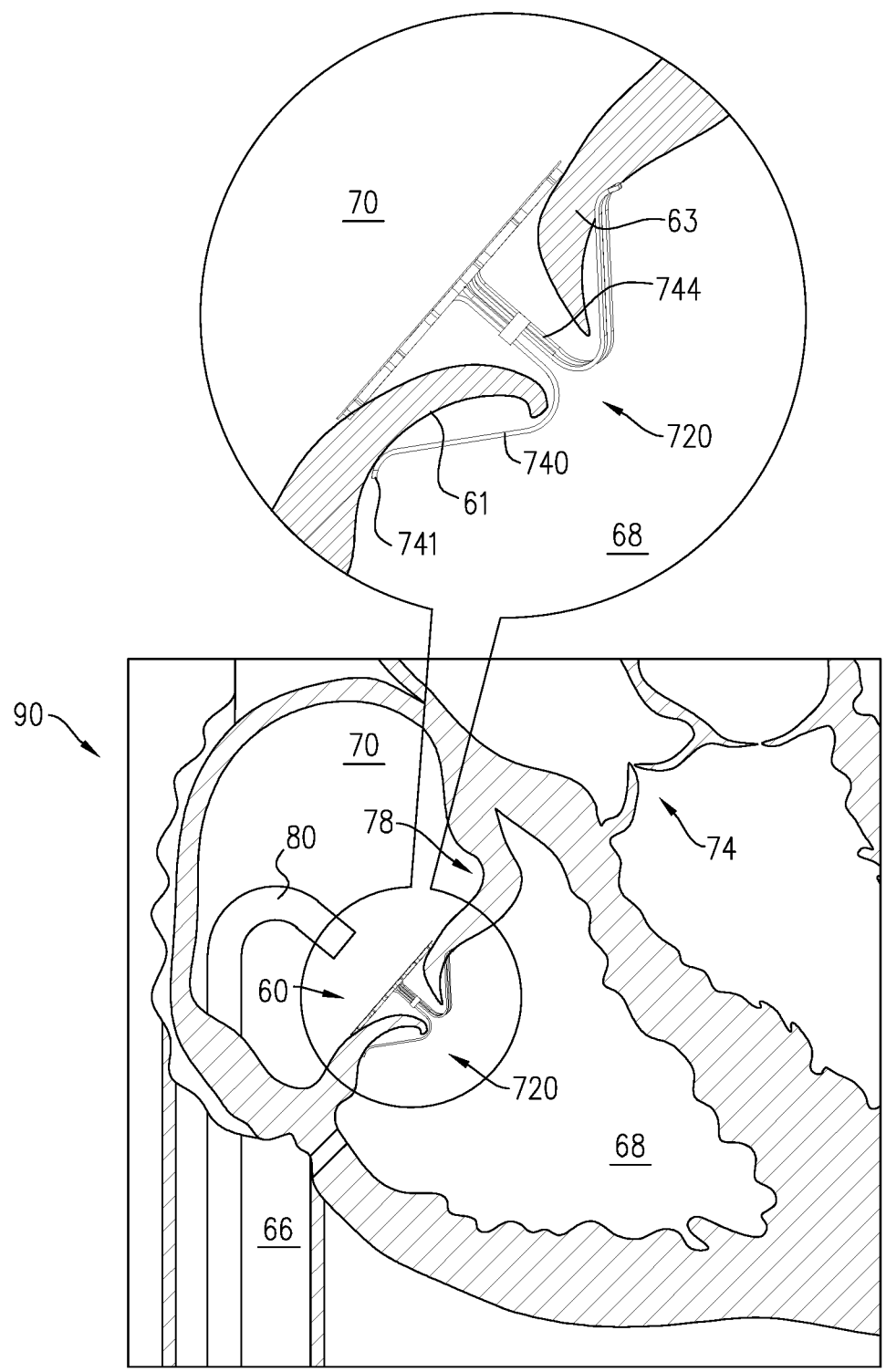
FIGS. 16-17 are schematic illustrations showing the leaflet support implanted at the tricuspid valve, in accordance with some applications of the present invention.
Figure 17:
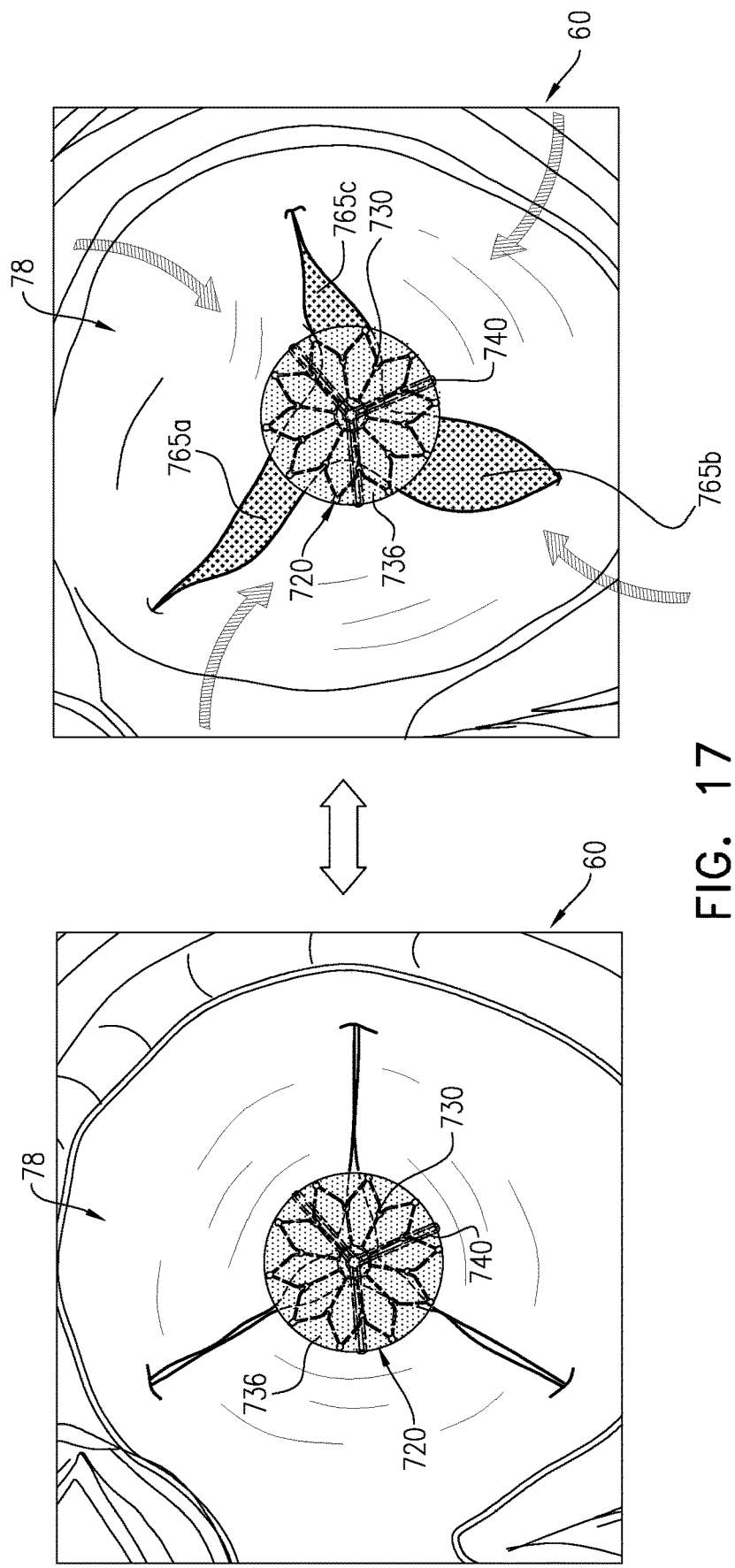

Reference is made to FIGS. 16-17, which are schematic illustrations showing leaflet support 720 implanted at tricuspid valve 60, in accordance with some applications of the invention.

As shown in FIG. 16, support 720 is deployed such that frame 730 is disposed upstream of annulus 48 of tricuspid valve 60. Similarly to frame 30 of support 20 described hereinabove, frame 730 is placed against tissue of right atrium 70 of heart 90. However, in contrast to frame 30, frame 730 does not comprise an annulus-fitting zone. In further contrast to frame 30, frame 730 is typically sized to not reach annulus 48 when implanted at the native valve. For such applications, a greatest width (e.g., a greatest diameter) of the ring formed by frame 730 (measured transverse to a central axis d718 of support 720) is less than the greatest width of frames 30, 30', 130, 230, 330, 430, 530, 630. For example, the greatest width of the ring may be greater than 10 mm (e.g., greater than 20 mm, e.g., greater than 30 mm, e.g., greater than 40 mm, e.g., greater than 50 mm) and/or less than 60 mm (e.g., less than 50 mm, e.g., less than 40 mm, e.g., less than 30 mm, e.g., less than 20 mm). Further, a greatest width of support 720 as a whole (measured transverse to axis d718) may be greater than 10 mm (e.g., greater than 20 mm, e.g., greater than 30 mm, e.g., greater than 40 mm, e.g., greater than 50 mm, e.g., greater than 60 mm, e.g., greater than 70 mm, e.g., greater than 80 mm, e.g., greater than 90 mm) and/or less than 100 mm (e.g., less than 90 mm, e.g., less than 80 mm, e.g., less than 70 mm, e.g., less than 60 mm, e.g., less than 50 mm, e.g., less than 40 mm, e.g., less than 30 mm, e.g., less than 20 mm).

In further contrast to support 20, support 720 is shown such that cusps of native leaflets 61, 63 are captured between frame 730 and legs 740. That is, leg end-portions 741 abut leaflets 61, 63 at a greater distance from frame 730 than were they disposed prior to implantation (FIGS. 15A-C). In this way, shape-memory of legs 740 may cause tissue of the native valve (e.g., cusps of native leaflets 61, 63) to be squeezed between the legs and frame 730. It is hypothesized by the inventors that squeezing tissue of the native valve between legs 740 and frame 730 facilitates fastening support 720 to the native valve.

Support 720 being fastened to the native valve by squeezing tissue between legs 740 and frame 730 stands in contrast to the manner in which supports 20, 420, 520, 620 are fastened to the native valve. That is, instead of squeezing tissue of the native valve, supports 20, 420, 520, 620 are typically implanted such that frame 30, 430, 530, 630 abuts annulus 48. Since frame 30, 430, 530, 630 (e.g., annulus-fitting zone 33, 433, 533, 633 thereof) is typically sized to fit annulus 48 of the native valve, it is hypothesized by the inventors that abutment of the frame to the annulus may be sufficient to inhibit downstream migration of supports 20, 420, 520, 620. Similarly, legs 40, 440, 540, 640 of supports 20, 420, 520, 620 have a span that is sufficient to inhibit upstream migration of the supports. Supports 20, 420, 520, 620 therefore typically do not require immobilization or gripping of leaflets, and are therefore typically not configured to do so.

The left pane of FIG. 17 shows tricuspid valve 60 during ventricular systole, and the right pane of FIG. 17 shows the tricuspid valve during ventricular diastole. It is hypothesized by the inventors that implantation of leaflet support 720 at tricuspid valve 60 may facilitate treatment of different pathological processes effecting heart 90. For example, in some cases, one or more of the native leaflets may flail or blood may regurgitate from right ventricle 68 into right atrium 70 (e.g., during ventricular systole). Similarly to support 20, it is hypothesized by the inventors that upon implantation of support 720 at the native valve, barrier 736 and/or frame 730 may obstruct flailing and/or regurgitation.

Supports 20, 420, 520, and 620 are hypothesized by the inventors to reduce valve regurgitation by inhibiting the native leaflets from flailing into the atrium during ventricular systole, while allowing the leaflets to deflect into the ventricle during ventricular diastole, e.g., as they would in the absence of the support. In contrast, support 720 is hypothesized by the inventors to reduce valve regurgitation by restraining the edges of the leaflets close to each other, so as to configure the leaflets into a multi-orifice arrangement. Therefore, support 720 is configured to squeeze the native leaflets between legs 740 and frame 730 of support 720 in order to grip the leaflets, while supports 20, 420, 520, and 620 are typically not configured in this manner. The right-side frame of FIG. 17 shows a portion of the native leaflets having deflected downstream during ventricular diastole, to a lesser degree than as shown in the right pane of FIG. 5.

As described hereinabove, support 720 is configured to configure the leaflets into a multi-orifice arrangement. That is, a secondary aperture 765 (e.g., three secondary apertures 765a, 765b, 765c for a trileaflet valve such as the tricuspid valve, or two secondary apertures for a bileaflet valve, such as the mitral valve) typically open between the native leaflets, radially outward from frame 730, as heart 90 cycles from ventricular systole to ventricular diastole. Arrows indicate antegrade blood flow from right atrium 70 to right ventricle 68, through secondary apertures 765a, 765b, 765c. It is hypothesized by the inventors that, for some applications, the smaller size of frame 730 compared with that of frames 30, 430, 530, 630 may further facilitate antegrade blood flow through secondary apertures 765.

Reference is made to FIGS. 18A-C and 20A-C, which are schematic illustrations showing perspective views of respective leaflet supports 820, 920, in accordance with some applications of the invention.

As shown, leaflet supports 820, 920 are each in certain ways similar to leaflet support 20 described hereinabove. Components that are identically named between the leaflet supports typically share similar features and serve similar functions as each other. As such, leaflet supports 820 and 920 will first be jointly described in relation to leaflet support 20, after which differences between leaflet supports 820 and 920 will be described.

Figure 18A:
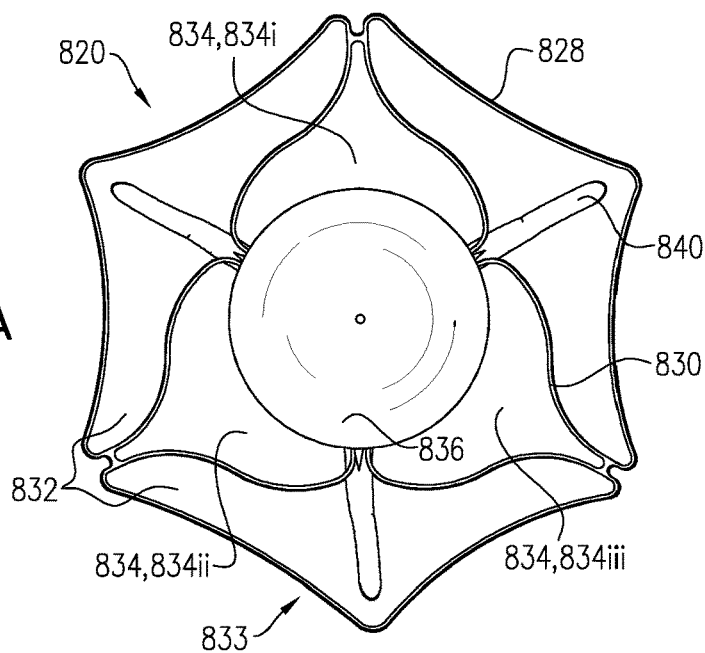
FIGS. 18A-C are schematic illustrations showing different perspective views of a leaflet support, in accordance with some applications of the present invention.
Figure 20A:
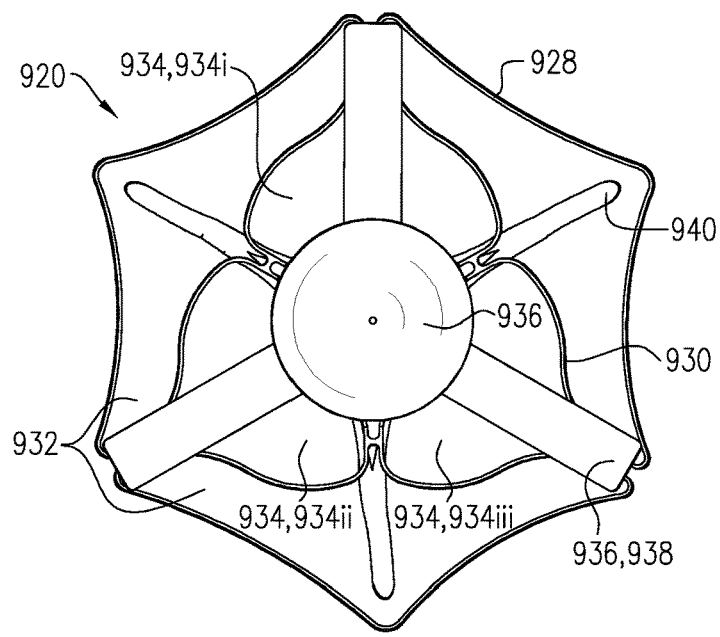
FIGS. 20A-C are schematic illustrations showing different perspective views of a leaflet support, in accordance with some applications of the present invention.

Similarly to leaflet support 20, each of leaflet supports 820, 920 comprises a frame 830, 930 that defines an array of adjoining cells 832, 932 and an aperture 834, 934 between an upstream side 822, 922 and a downstream side 824, 924 of the frame. Similarly to frame 30, which extends radially inward from an outer ring-perimeter 28, frames 830, 930 extend radially inward from outer frame-perimeter 828, 928 (FIGS. 18A, 20A).

However, in contrast to frame 30 of leaflet support 20, frames 830, 930 are not necessarily ring-shaped. Therefore, whereas frame 30 extends radially outward from inner ring-perimeter 26 that defines aperture 34, frames 830, 930 each comprise a plurality of aperture-surrounding struts 844, 944 that extend radially inwardly and in a downstream direction from outer frame-perimeter 828 (FIGS. 18B-C and 20B-C).

Figure 18B:
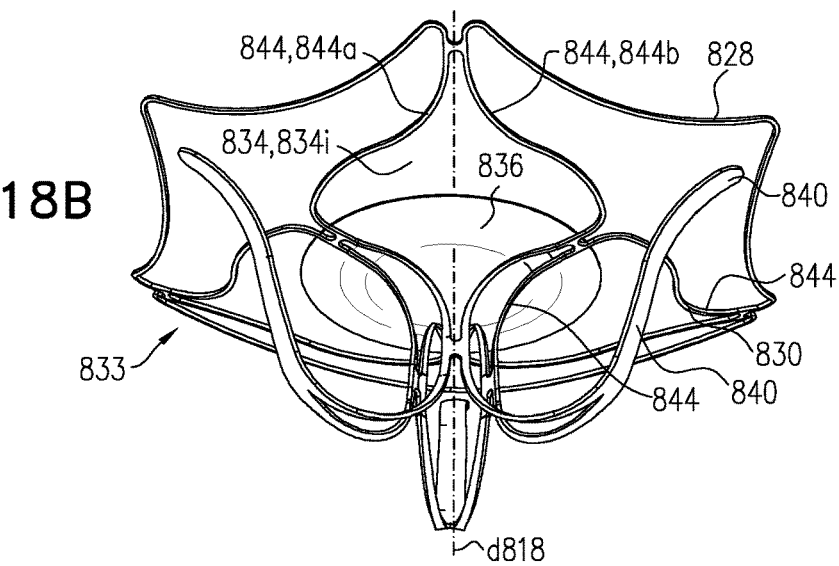
Figure 20B:
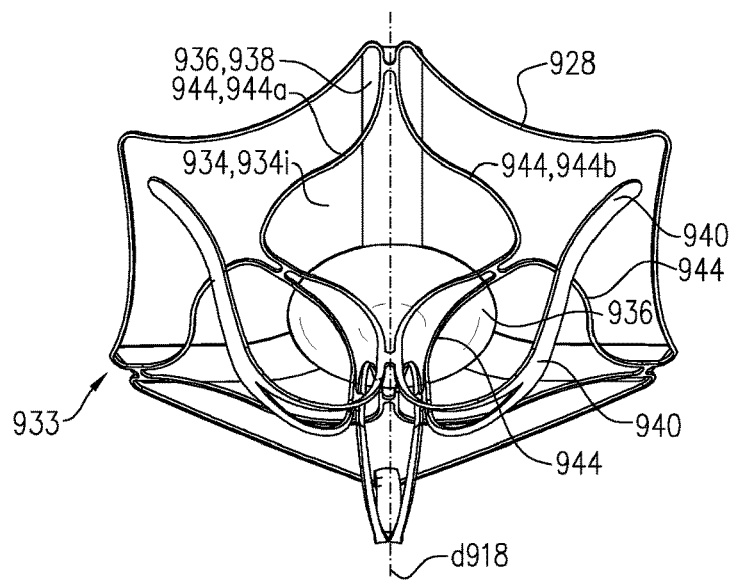

For some applications, and as shown in FIGS. 18B and 20B, two aperture-surrounding struts (e.g., 844a and 844b, 944a and 944b) surround each aperture 834, 934. For some such applications, frame 830, 930 defines a plurality of apertures (834i, 834ii, 834iii, or 934i, 934ii, 934iii), such that each aperture is surrounded by at least two aperture-surrounding struts (FIGS. 18A, 20A).

Figure 18C:
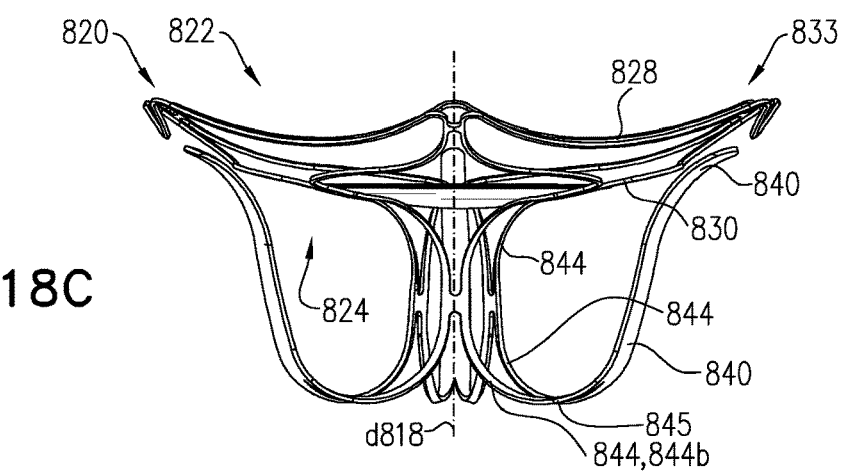
Figure 20C:
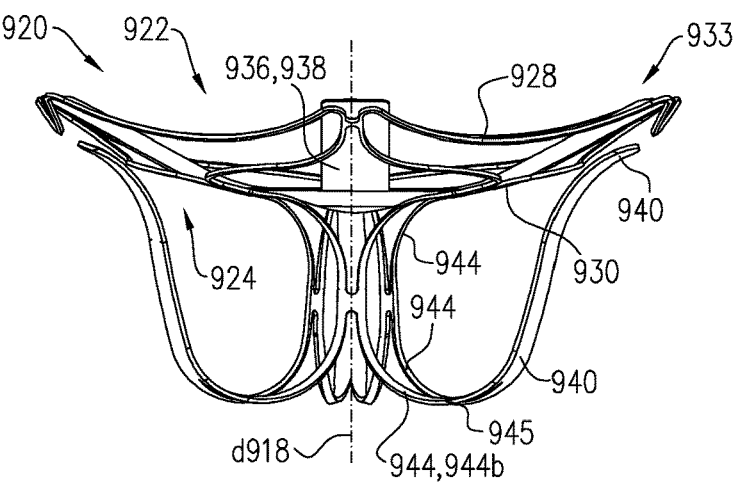

Further similarly to leaflet support 20, leaflet supports 820 and 920 comprise ventricular legs 840, 940 that extend radially outward and upstream, towards frame 830, 930 (FIGS. 18C and 20C). Ventricular legs 840, 940 typically afford the native leaflets a range of motion in which to deflect during the cardiac cycle, as described hereinbelow with reference to FIGS. 19 and 21.

Similarly to the application described hereinabove with reference to FIGS. 1A-5, in which legs 40 are connected to frame 30 via connecting portion 44, legs 840, 940 are typically connected to frame 830, 930 via aperture-surrounding struts 844, 944. For some applications, and as shown, each ventricular leg 840, 940 extends radially outward, and toward frame 830, 930 from a downstream end 845, 945 of aperture-surrounding strut 844, 944. For example, each leg 840, 940 may extend radially outward from a pair of the aperture-surrounding struts 844, 944 (e.g., such that the pair of aperture-surrounding struts meet at downstream end 845, 945). For some such applications, each of the pair of aperture-surrounding struts partially surrounds a different aperture 834, 934 (FIGS. 18B-C and 20B-C).

Further similarly to leaflet support 20, leaflet supports 820 and 920 respectively comprise a barrier 836, 936 that is impermeable to blood flow. Barrier 836, 936 is coupled to frame 830, 930 in a manner that obstructs blood flow through aperture 834, 934 (e.g., by at least partially covering at least one of apertures 834i, 834ii, 834iii or 934i, 934ii, 934iii). For example, and as shown in FIGS. 18A and 20A, barrier 836, 936 is coupled to frame 830, 930 in a manner that partially covers more than one of apertures 834, 934.

For some applications, and further similarly to leaflet support 20, barrier 836, 936 is coupled to frame 830, 930 in a manner that also at least partially covers the array of cells 832, 932 (not shown). For example, and as shown, barrier 836, 936 may be coupled to frame 830, 930 in a manner that at least partially covers a plurality of cells 832, 932 (e.g., each cell of frame 830, 930).

A feature that distinguishes between leaflet supports 820 and 920 lies in the shape of respective barriers 836, 936. Barrier 836 of leaflet support 820 is in many ways similar to barrier 36 of leaflet support 20. For example, barrier 836 may define a barrier-fitting portion as described hereinabove with reference to barrier 36 of leaflet support 20, mutatis mutandis.

In contrast to barrier 836, barrier 936 defines a radial strip 938 that extends between central axis d918 and outer frame-perimeter 928. That is, radial strip 938 may not reach central axis d918 and/or outer frame-perimeter 928, yet the radial strip extends between the central axis and the outer frame-perimeter. In this way, radial strip 938 extends radially inwardly toward central axis d918 and radially outwardly toward the outer frame-perimeter. For some applications, radial strip 938 may be sized to correspond to dimensions of the native heart valve. For example, radial strip 938 may extend at least two thirds of a radial distance from central axis d918 to outer frame-perimeter 928.

For some applications, barrier 936 defines more than one radial strip 938 (e.g., corresponding to a number of commissures of a native heart valve). For some such applications, each radial strip 938 is positioned to align with a respective commissure of the native heart valve. For example, and as shown, a leaflet support that is configured to be implanted at tricuspid valve 60 may have exactly three radial strips 938.

Reference is made to FIGS. 19 and 21, which include schematic illustrations showing leaflet supports 820, 920 respectively implanted at tricuspid valve 60, in accordance with some applications of the invention. The left panes of FIGS. 19 and 21 show tricuspid valve 60 during ventricular systole, and the right panes of FIGS. 19 and 21 show the tricuspid valve during ventricular diastole.

Similarly to as described hereinabove with reference to leaflet support 20, each cell 832, 932 and therefore frame 830, 930 as a whole, is configured to facilitate passage of blood therethrough. Therefore, when leaflet support 820, 920 is implanted at tricuspid valve 60, blood may flow between upstream side 822, 922 and downstream side 824, 924 of the frame (e.g., during ventricular diastole).

Further similarly to leaflet support 20, leaflet supports 820 and 920 are typically sized such that frame 830, 930 fits annulus 48 of tricuspid valve 60 (e.g., such that frame 830, 930 (e.g., an annulus-fitting zone 833, 933 thereof) can be placed against the annulus). A greatest width (measured transverse to axis d818, d918) of frame 830, 930 is also typically similar to the greatest width of frame 30. For some applications, the greatest width of frame 830, 930 is between 10 mm and 100 mm. For some such applications, the greatest width of frame 830, 930 is less than 60 mm. Alternatively or additionally, the greatest width of frame 830, 930 may be greater than 40 mm.

Further similarly to leaflet support 20, upon implantation of leaflet support 820, 920 at the native valve, barrier 836, 936 and/or frame 830, 930 are typically disposed such that they reduce flailing of native leaflets of the heart into an atrium of the heart, and barrier 836, 936 may obstruct regurgitation of blood (e.g., during ventricular systole). Thus, leaflet support 820, 920 may be desirably implanted in the heart of a subject experiencing leaflet flailing and/or regurgitation at a portion of a native heart valve that is covered by barrier 836, 936 when the leaflet support is implanted at the native valve.

Furthermore, barrier 836, 936 is typically sized and positioned to facilitate antegrade blood flow during ventricular diastole. Arrows in the right panes of FIGS. 19 and 21 indicate antegrade blood flow from the right atrium on upstream side 22 of support 820, 920 to the right ventricle on downstream side 824, 924 of frame 830, 930.

For some applications, and as shown in FIG. 19, barrier 836 of leaflet support 820 only partially covers apertures 834. As such, blood may flow antegrade through apertures 834 and/or cells 832 of leaflet support 820, during ventricular diastole.

In contrast to barrier 836, radial strips 938 of leaflet support 920 extend radially outwardly toward outer frame-perimeter 928. Thus, leaflet support 920 may be desirably implanted in the heart of a subject experiencing leaflet flailing and/or regurgitation at a portion of a native heart valve that is covered by radial strips 938 when leaflet support 920 is implanted at the native valve. It is nonetheless desirable that radial strips 938 do not unduly obstruct antegrade blood flow during ventricular diastole. Radial strips 938 are therefore typically sized and positioned so as to allow for blood to flow between the radial strips (right pane of FIG. 21).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a native valve of a heart of a subject, the apparatus comprising a leaflet support, the leaflet support comprising:
   a frame having an upstream side and a downstream side, the frame:
      defining an array of adjoining cells, and an aperture between the upstream side and the downstream side, and
      configured to:
         be placed against an annulus of the heart, and
         facilitate blood flow, via the cells of the array of adjoining cells,
      between the upstream side and the downstream side;
   a barrier:
      made of material that is impermeable to blood flow, and
      coupled to the frame in a manner that obstructs blood flow through the aperture; and
   a plurality of ventricular legs, each ventricular leg extending radially outward and upstream, toward the frame,
   wherein the leaflet support is shaped to define a central longitudinal axis that is configured to pass through the material of the barrier throughout the cardiac cycle.

2. The apparatus according to claim 1, wherein each of the ventricular legs is coupled to the frame.

3. The apparatus according to claim 1, wherein each ventricular leg extends further radially outward than the barrier.

4. The apparatus according to claim 1, wherein the aperture is a first aperture, and the frame further defines a second aperture between the upstream side and the downstream side.

5. The apparatus according to claim 1, wherein:
   the aperture is a first aperture,
   the frame is shaped to define a second aperture between the upstream side and the downstream side, and
   the frame comprises a plurality of aperture-surrounding struts, at least two of the aperture-surrounding struts surrounding the first aperture and at least two of the aperture-surrounding struts surrounding the second aperture, the aperture-surrounding struts extending radially inwardly and in a downstream direction from an outer frame-perimeter of the frame.

6. The apparatus according to claim 5, wherein each ventricular leg extends radially outward from exactly two of the aperture-surrounding struts.

7. The apparatus according to claim 5, wherein each ventricular leg extends radially outward from a downstream end of at least one of the aperture-surrounding struts.

8. The apparatus according to claim 7, wherein each ventricular leg extends, from the downstream end of at least one of the aperture-surrounding struts:
   radially outward, and
   toward the frame.

9. The apparatus according to claim 7, wherein a respective end-portion of each ventricular leg faces the frame from a position that is:
radially outward of the barrier, and
downstream from the frame.

10. The apparatus according to claim 7, wherein, in an absence of tissue between the ventricular legs and the frame, a respective end-portion of each ventricular leg is disposed upstream from the frame.

11. The apparatus according to claim 7, wherein, in an absence of tissue between the ventricular legs and the barrier, a respective end-portion of each ventricular leg presses against the barrier.

12. The apparatus according to claim 1, wherein the barrier is coupled to the frame in a manner that at least partially covers at least one of the cells.

13. The apparatus according to claim 12, wherein the barrier is coupled to the frame in a manner that at least partially covers each cell of the frame.

14. The apparatus according to claim 1, wherein:
the frame defines an outer frame-perimeter, and
the barrier is shaped to define at least one radial strip, the at least one radial strip extending radially inwardly toward a central axis of the leaflet support and radially outwardly toward the outer frame-perimeter.

15. The apparatus according to claim 14, wherein the at least one radial strip extends at least two thirds of a radial distance from the central axis to the outer frame-perimeter.

16. The apparatus according to claim 14, wherein the at least one radial strip is a plurality of the radial strips.

17. The apparatus according to claim 16, wherein the plurality of the radial strips comprises exactly three of the radial strips.

18. The apparatus according to claim 16, wherein the plurality of the radial strips are positioned to each align with a respective commissure of the native valve of the heart of the subject and to reduce flailing of native leaflets of the heart into an atrium of the heart.

19. The apparatus according to claim 1, wherein:
the aperture defines an aperture area, and
the barrier obstructs blood flow through the aperture by covering a portion of the aperture area.

20. The apparatus according to claim 1, further comprising a barrier-delivery tool, the barrier-delivery tool configured to:
reversibly engage the barrier, and
while the frame is disposed at the native valve, transluminally:
position the barrier with respect to the frame, and
couple the barrier to the frame in the manner that obstructs blood flow through the aperture.

21. The apparatus according to claim 1, wherein the barrier is circular or elliptical.

22. The apparatus according to claim 1, wherein the barrier is "D"-shaped.

23. The apparatus according to claim 1, wherein the adjoining cells of the array are arranged to shape the frame as a ring having an inner ring-perimeter that defines the aperture.

24. The apparatus according to claim 1, wherein the central longitudinal axis of the leaflet support passes through a center point of the barrier.

25. The apparatus according to claim 1, wherein the barrier is offset with respect to the central longitudinal axis of the leaflet support.

26. The apparatus according to claim 1, wherein the barrier has a transverse plane that is coplanar with a transverse plane of the aperture, and wherein the barrier covers at least a portion of the aperture.

27. The apparatus according to claim 1, wherein the leaflet support is configured to facilitate functioning of the native valve while the leaflet support is implanted at the native valve, by allowing leaflets of the native valve to deflect as the heart cycles between ventricular systole and ventricular diastole.

28. The apparatus according to claim 1, wherein the barrier is planar.

29. The apparatus according to claim 28, wherein the barrier is triangular.

30. The apparatus according to claim 28, wherein the barrier is shaped as a disc.

* * * * *